(12) United States Patent
Whiting et al.

(10) Patent No.: US 8,029,470 B2
(45) Date of Patent: Oct. 4, 2011

(54) TRANSMEMBRANE ACCESS SYSTEMS AND METHODS

(75) Inventors: James S. Whiting, Los Angeles, CA (US); Neal L. Eigler, Pacific Palisades, CA (US); John L. Wardle, San Clemente, CA (US); Werner Hafelfinger, Thousand Oaks, CA (US); Brian Mann, Edgartown, MA (US)

(73) Assignee: Pacesetter, Inc., Sylmar, CA (US)

( * ) Notice: Subject to any disclaimer, the term of this patent is extended or adjusted under 35 U.S.C. 154(b) by 2104 days.

(21) Appl. No.: 10/956,899

(22) Filed: Sep. 30, 2004

(65) Prior Publication Data

US 2006/0074398 A1    Apr. 6, 2006

(51) Int. Cl.
*A61M 5/178* (2006.01)
(52) U.S. Cl. .............................. 604/164.01; 604/164.09
(58) Field of Classification Search ............ 604/164.01–170.03, 264, 510
See application file for complete search history.

(56) References Cited

U.S. PATENT DOCUMENTS

| | | | |
|---|---|---|---|
| 4,342,313 A | 8/1982 | Chittenden | |
| 4,405,314 A * | 9/1983 | Cope | 604/510 |
| 4,791,937 A | 12/1988 | Wang | |
| 4,986,814 A | 1/1991 | Burney et al. | |
| 4,998,975 A | 3/1991 | Cohen et al. | |
| 4,998,977 A | 3/1991 | Preiss et al. | |
| 5,115,814 A | 5/1992 | Griffith et al. | |
| 5,190,528 A | 3/1993 | Fonger et al. | |
| 5,250,038 A | 10/1993 | Melker et al. | |
| 5,312,341 A | 5/1994 | Turi | |
| 5,324,304 A | 6/1994 | Rasmussen | |
| 5,396,902 A | 3/1995 | Brennan et al. | |
| 5,409,469 A | 4/1995 | Schaerf | |
| 5,415,639 A | 5/1995 | VandenEinde et al. | |

(Continued)

FOREIGN PATENT DOCUMENTS

WO    WO 03/077733    9/2003

(Continued)

OTHER PUBLICATIONS

PCT International Preliminary Report on Patentability and Written Opinion of the International Searching Authority (PCT/US2005/023720 Mailed Aug. 29, 2007).

(Continued)

*Primary Examiner* — Nicholas D Lucchesi
*Assistant Examiner* — Gerald Landry, II
(74) *Attorney, Agent, or Firm* — Grant Anderson LLP

(57) ABSTRACT

Systems and methods for penetrating a tissue membrane to gain access to a target site are disclosed. In some examples, systems and methods for accessing the left atrium from the right atrium of a patient's heart are carried out by puncturing the intra-atrial septal wall. One embodiment provides a system for transseptal cardiac access that includes a stabilizer sheath having a side port, a shaped guiding catheter configured to exit the side port and a tissue penetration member disposed within and extendable from the distal end of the guide catheter. The tissue penetration member may be configured to penetrate tissue upon rotation and may be coupled to a distal portion of a torqueable shaft. In some embodiments, the stabilizer sheath and shaped guiding catheter may be moved relative to the patient's body structure and relative to each other so that a desired approach angle may be obtained for the tissue penetration member with respect to the target tissue.

7 Claims, 27 Drawing Sheets

U.S. PATENT DOCUMENTS

| | | | |
|---|---|---|---|
| 5,427,119 | A | 6/1995 | Swartz et al. |
| 5,488,960 | A | 2/1996 | Toner |
| 5,497,774 | A | 3/1996 | Swartz et al. |
| 5,617,854 | A | 4/1997 | Munsif |
| 5,628,316 | A | 5/1997 | Swartz et al. |
| 5,640,955 | A | 6/1997 | Ockuly et al. |
| 5,662,119 | A | 9/1997 | Brennan et al. |
| 5,713,867 | A | 2/1998 | Morris |
| 5,715,818 | A | 2/1998 | Swartz et al. |
| 5,725,512 | A | 3/1998 | Swartz et al. |
| 5,800,413 | A | 9/1998 | Swartz et al. |
| 5,807,306 | A | 9/1998 | Shapland et al. |
| 5,807,326 | A | 9/1998 | O'Neill et al. |
| 5,807,395 | A | 9/1998 | Mulier et al. |
| 5,810,730 | A | 9/1998 | Swartz et al. |
| 5,814,027 | A | 9/1998 | Hasset et al. |
| 5,814,028 | A | 9/1998 | Swartz et al. |
| 5,830,222 | A | 11/1998 | Makower |
| 5,840,027 | A | 11/1998 | Swartz et al. |
| 5,861,003 | A | 1/1999 | Latson et al. |
| 5,871,531 | A | 2/1999 | Struble |
| 5,873,842 | A | 2/1999 | Brennan et al. |
| 5,879,296 | A | 3/1999 | Ockuly et al. |
| 5,902,289 | A | 5/1999 | Swartz et al. |
| 5,902,329 | A | 5/1999 | Hoffman et al. |
| 5,902,331 | A | 5/1999 | Bonner et al. |
| 5,935,160 | A | 8/1999 | Auricchio et al. |
| 5,968,010 | A | 10/1999 | Waxman et al. |
| 5,976,174 | A | 11/1999 | Ruiz |
| 6,004,280 | A | 12/1999 | Buck et al. |
| 6,024,756 | A | 2/2000 | Huebsch et al. |
| 6,068,638 | A | 5/2000 | Makower |
| 6,090,084 | A | 7/2000 | Hasset et al. |
| 6,123,084 | A * | 9/2000 | Jandak et al. ............... 128/898 |
| 6,132,456 | A | 10/2000 | Sommer et al. |
| 6,152,144 | A | 11/2000 | Lesh et al. |
| 6,156,018 | A | 12/2000 | Hasset |
| 6,190,354 | B1 | 2/2001 | Sell et al. |
| 6,197,001 | B1 | 3/2001 | Wilson et al. |
| 6,200,303 | B1 | 3/2001 | Verrior et al. |
| 6,217,558 | B1 | 4/2001 | Zandini et al. |
| 6,223,087 | B1 | 4/2001 | Williams |
| 6,234,958 | B1 | 5/2001 | Snoke et al. |
| 6,241,728 | B1 | 6/2001 | Gaiser et al. |
| 6,245,054 | B1 | 6/2001 | Fuimaono et al. |
| 6,277,107 | B1 | 8/2001 | Lurie et al. |
| 6,278,897 | B1 | 8/2001 | Rutten et al. |
| 6,280,433 | B1 | 8/2001 | McIvor et al. |
| 6,328,699 | B1 | 12/2001 | Eigler et al. |
| 6,379,346 | B1 | 4/2002 | McIvor et al. |
| 6,402,772 | B1 | 6/2002 | Amplatz et al. |
| 6,408,214 | B1 | 6/2002 | Williams et al. |
| 6,440,120 | B1 | 8/2002 | Maahs |
| 6,456,889 | B2 | 9/2002 | Pianca et al. |
| 6,456,890 | B2 | 9/2002 | Piance et al. |
| 6,497,698 | B1 | 12/2002 | Fonger et al. |
| 6,526,302 | B2 | 2/2003 | Hasset |
| 6,540,755 | B2 | 4/2003 | Ockuly et al. |
| 6,562,049 | B1 | 5/2003 | Norlander et al. |
| 6,569,182 | B1 | 5/2003 | Balceta et al. |
| 6,579,311 | B1 | 6/2003 | Makower |
| 6,599,288 | B2 | 7/2003 | Maguire et al. |
| 6,602,278 | B1 | 8/2003 | Thompson et al. |
| 6,623,449 | B2 | 9/2003 | Paskar |
| 6,650,923 | B1 | 11/2003 | Lesh et al. |
| 6,656,166 | B2 | 12/2003 | Lurie et al. |
| 6,676,650 | B1 | 1/2004 | Magovern et al. |
| 6,697,677 | B2 | 2/2004 | Dahl et al. |
| 6,733,500 | B2 | 5/2004 | Kelley et al. |
| 6,755,812 | B2 | 6/2004 | Peterson et al. |
| 6,869,414 | B2 | 3/2005 | Simpson et al. |
| 7,056,294 | B2 | 6/2006 | Khairkhahan et al. |
| 7,449,010 | B1 | 11/2008 | Hayase |
| 7,678,081 | B2 | 3/2010 | Whiting |
| 2002/0026175 | A1 * | 2/2002 | Paskar ............... 604/528 |
| 2002/0143255 | A1 | 10/2002 | Webler et al. |
| 2002/0169377 | A1 * | 11/2002 | Khairkhahan et al. ........ 600/433 |
| 2003/0032936 | A1 * | 2/2003 | Lederman ............... 604/507 |
| 2003/0130598 | A1 * | 7/2003 | Manning et al. ............... 600/585 |
| 2003/0144657 | A1 * | 7/2003 | Bowe et al. ............... 606/41 |
| 2003/0236492 | A1 | 12/2003 | Honebrink |
| 2004/0054335 | A1 * | 3/2004 | Lesh et al. ............... 604/264 |
| 2004/0054355 | A1 | 3/2004 | Gerbi et al. |
| 2004/0059280 | A1 * | 3/2004 | Makower et al. ............... 604/8 |
| 2004/0059351 | A1 | 3/2004 | Eigler et al. |
| 2004/0092879 | A1 | 5/2004 | Kraus et al. |
| 2004/0147969 | A1 | 7/2004 | Mann et al. |
| 2004/0215185 | A1 | 10/2004 | Truckai et al. |
| 2006/0009715 | A1 | 1/2006 | Khairkhahan et al. |
| 2006/0009737 | A1 | 1/2006 | Whiting et al. |
| 2006/0074398 | A1 | 4/2006 | Whiting et al. |
| 2006/0079787 | A1 | 4/2006 | Whiting et al. |

FOREIGN PATENT DOCUMENTS

| | | |
|---|---|---|
| WO | WO 03/077733 A2 | 9/2003 |
| WO | WO 03/077733 A3 | 9/2003 |

OTHER PUBLICATIONS

PCT International Search Report (PCT/US05/35256 mailed Apr. 24, 2007).

Office Action mailed on Jan. 23, 2009 for U.S. Appl. No. 10/889,319, filed Jul. 12, 2004 published as: US 2006/0009737 A1 on Jan. 12, 2006.

Office Action mailed on Jul. 16, 2008 for U.S. Appl. No. 10/889,319, filed Jul. 12, 2004 published as: US 2006/0009737 A1 on Jan. 12, 2006.

Office Action mailed on Dec. 28, 2007 for U.S. Appl. No. 10/889,319, filed Jul. 12, 2004 published as: US 2006/0009737 A1 on Jan. 12, 2006.

Office Action mailed on Jun. 8, 2007 for U.S. Appl. No. 10/889,319, filed Jul. 12, 2004 published as: US 2006/0009737 A1 on Jan. 12, 2006.

Office Action mailed on Dec. 18, 2006 for U.S. Appl. No. 10/889,319, filed Jul. 12, 2004 published as: US 2006/0009737 A1 on Jan. 12, 2006.

Office Action mailed on Jan. 12, 2009 for U.S. Appl. No. 11/203,624, filed Aug. 11, 2005 published as: US 2006/0079787 A1 on Apr. 13, 2006.

Office Action mailed on Jun. 25, 2009 for U.S. Appl. No. 11/203,624, filed Aug. 11, 2005 published as: US 2006/0079787 A1 on Apr. 13, 2006.

Office Action mailed on Feb. 9, 2009 for U.S. Appl. No. 11/239,174, filed Sep. 28, 2005 published as: US 2006/0079769 A1 on Apr. 13, 2006.

Office Action mailed on Jun. 30, 2008 for U.S. Appl. No. 11/239,174, filed Sep. 28, 2005 published as: US 2006/0079769 A1 on Apr. 13, 2006.

Office Action mailed on Apr. 16, 2009 for U.S. Appl. No. 11/394,149, filed Mar. 29, 2006 published as: US 2007/0083168 A1 on Apr. 12, 2007.

Office Action mailed on Oct. 26, 2009 for U.S. Appl. No. 10/889,319, filed: Jul. 12, 2004 published as: US 2006/0009737 A1 on Jan. 12, 2006.

Office Action mailed on Jun. 6, 2009 for U.S. Appl. No. 10/889,319, filed: Jul. 12, 2004 published as: US 2006/0009737 A1 on Jan. 12, 2006.

Office Action mailed on Feb. 17, 2010 for U.S. Appl. No. 11/203,624, filed: Aug. 11, 2005 published as: US 2006/0079787 A1 on Apr. 13, 2006.

Office Action mailed on Jul. 21, 2009 for U.S. Appl. No. 11/203,624, filed: Aug. 11, 2005 published as: US 2006/0079787 A1 on Apr. 13, 2006.

Office Action mailed on Jun. 23, 2009 for U.S. Appl. No. 11/239,174, filed: Sep. 28, 2005 published as: US 2006/0079769 A1 on Apr. 13, 2006.

Office Action mailed on Jan. 7, 2010 for U.S. Appl. No. 11/239,174, filed: Sep. 28, 2005 published as: US 2006/0079769 A1 on Apr. 13, 2006.

Office Action mailed on Dec. 28, 2009 for U.S. Appl. No. 11/394,149, filed Mar. 29, 2006 published as: US 2007/0083168 A1 on Apr. 12, 2007.

* cited by examiner

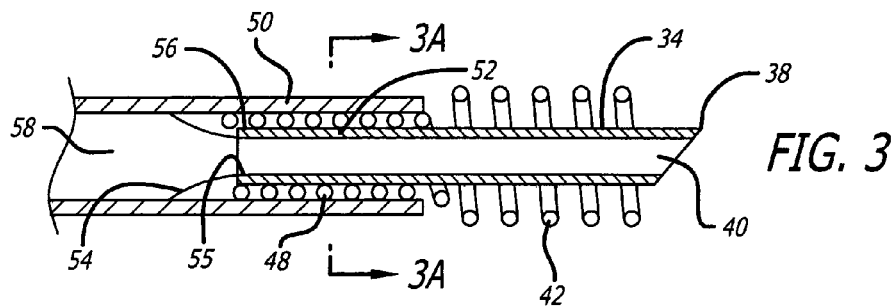
FIG. 3
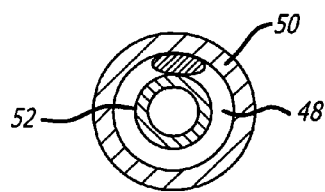
FIG. 3A
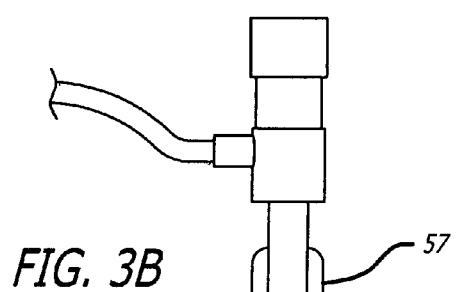
FIG. 3B
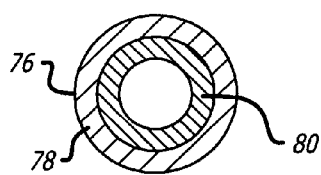
FIG. 3C
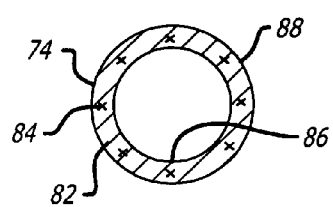
FIG. 3D
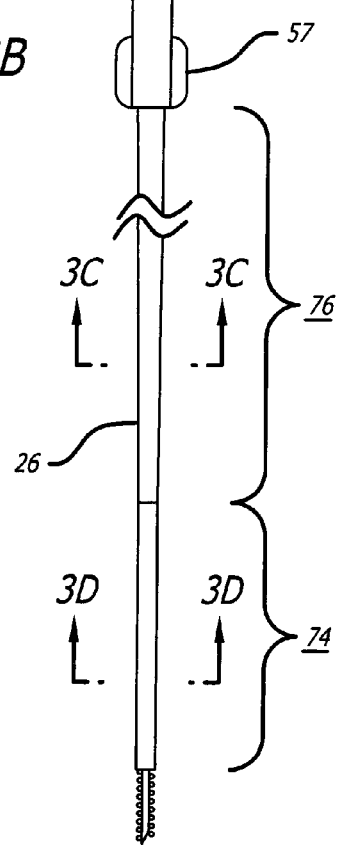

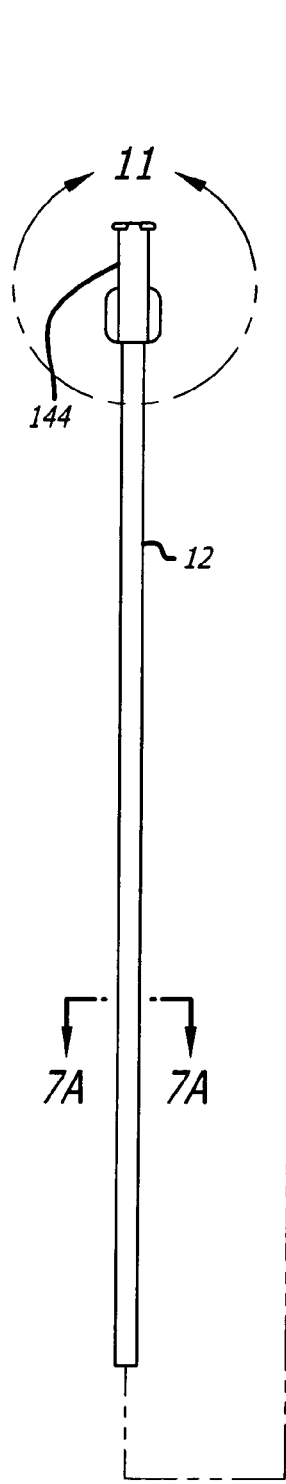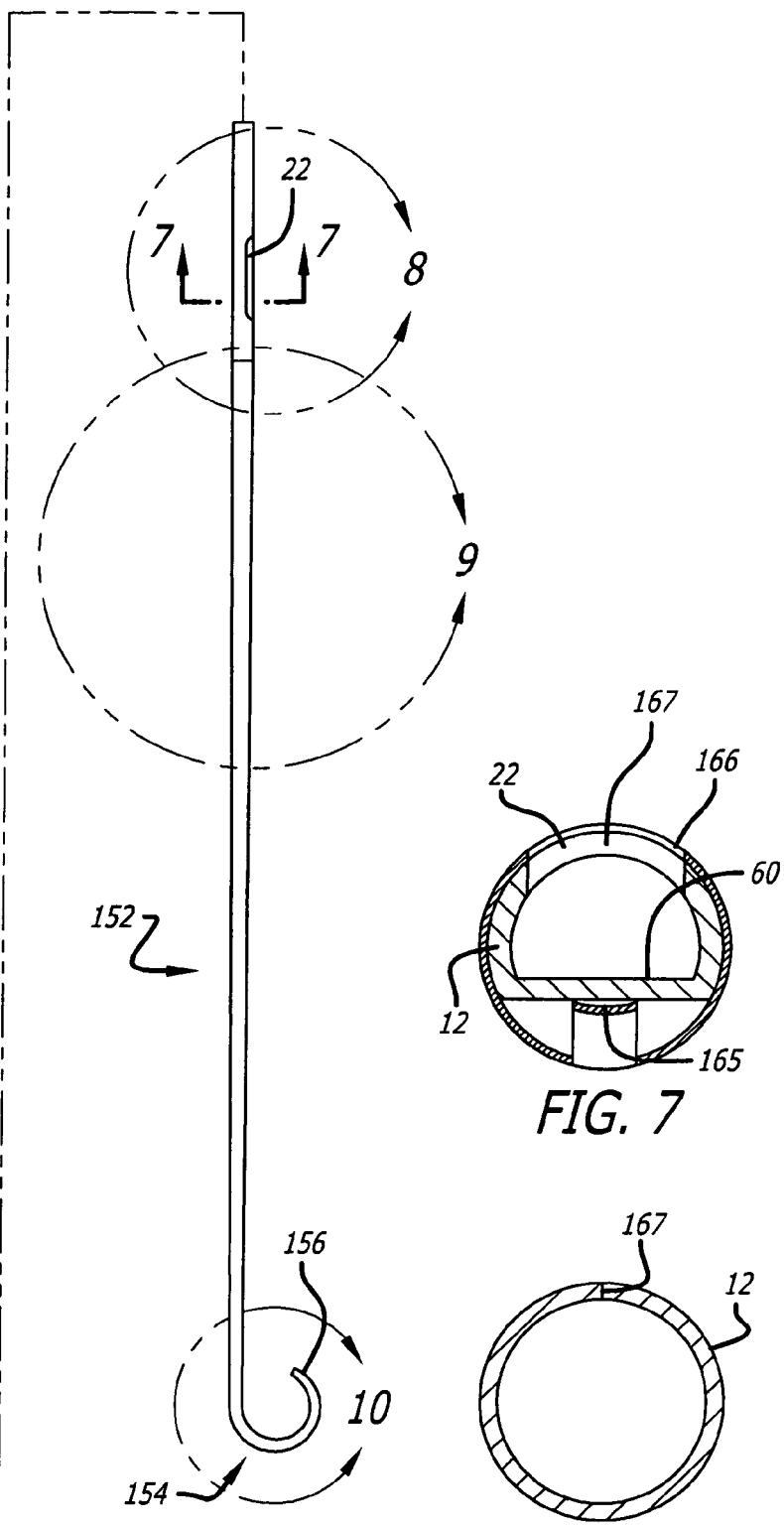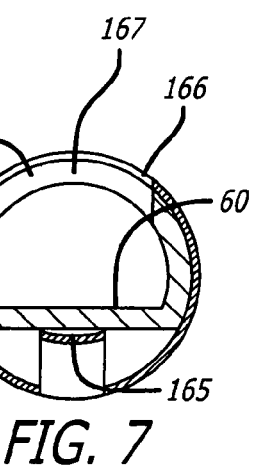
FIG. 6
FIG. 7
FIG. 7A

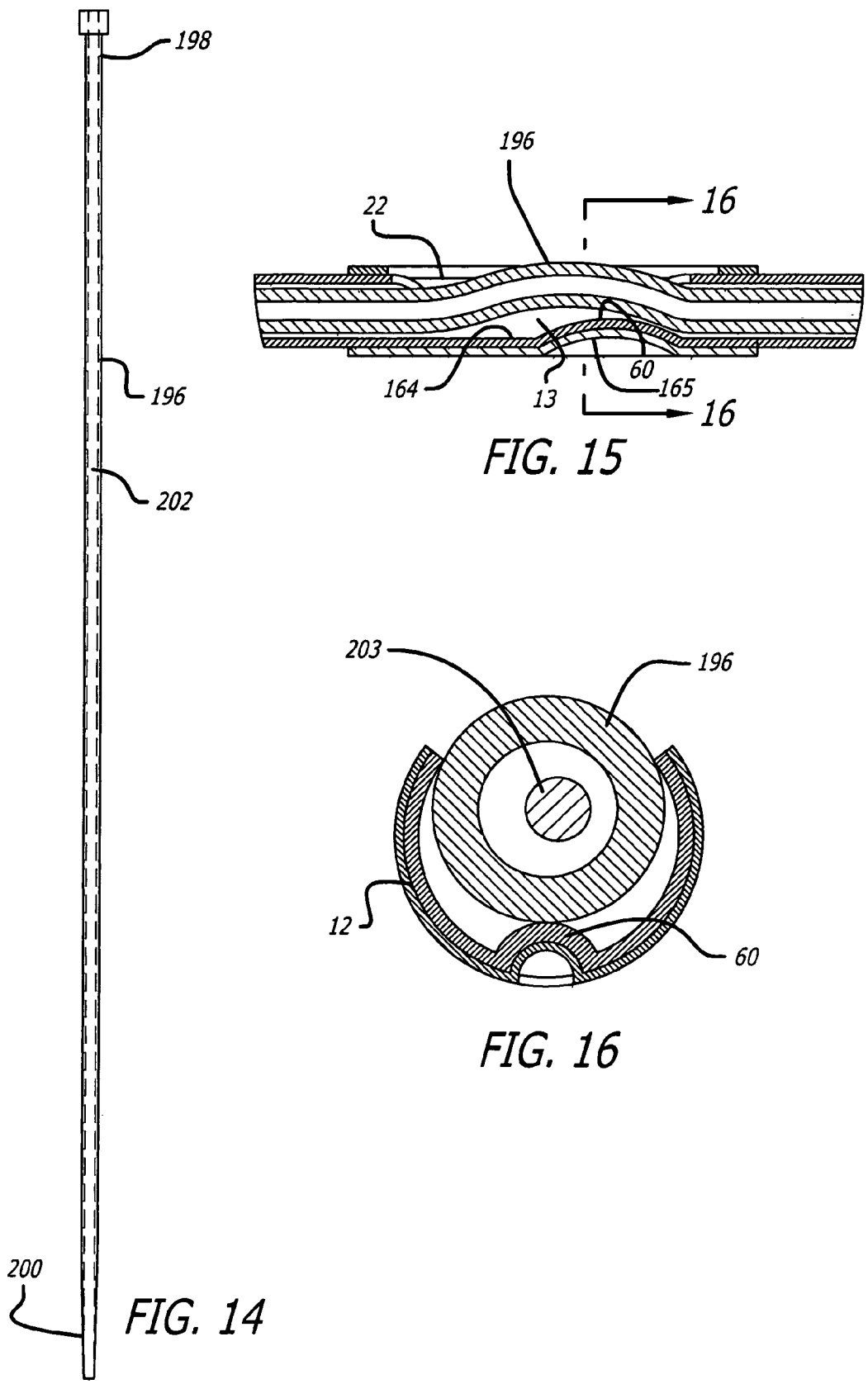

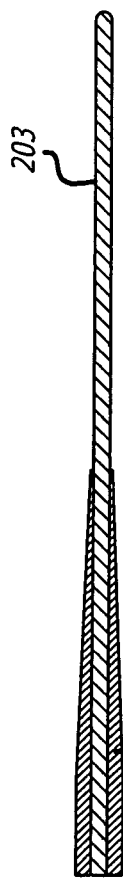
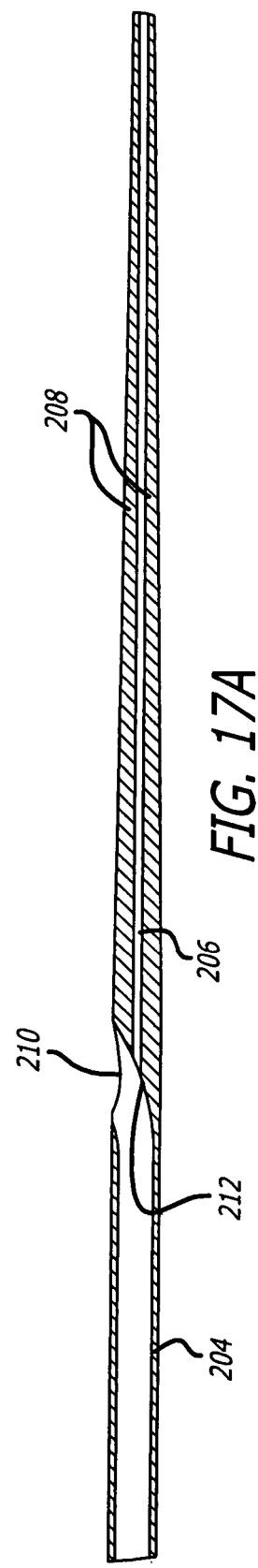
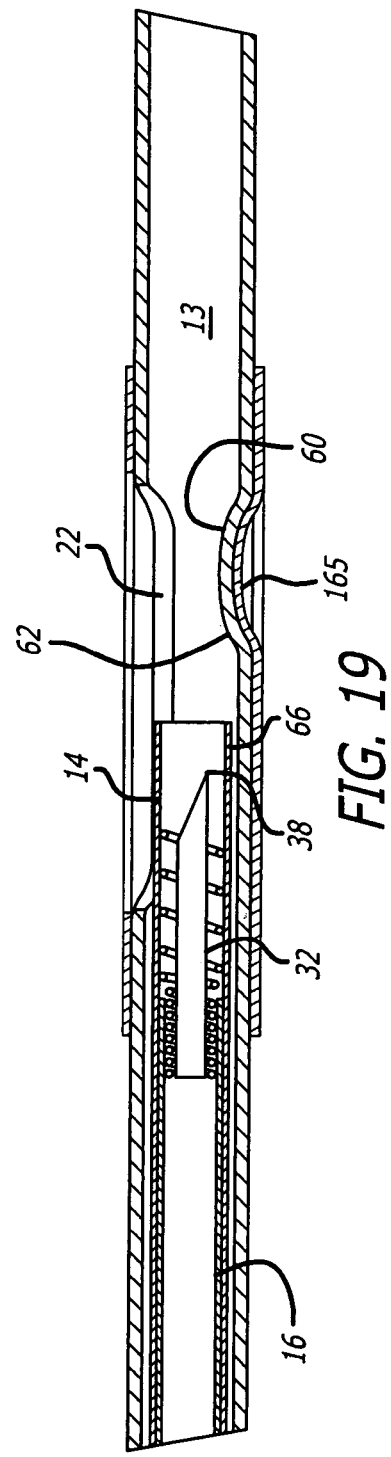
FIG. 17
FIG. 17A
FIG. 19

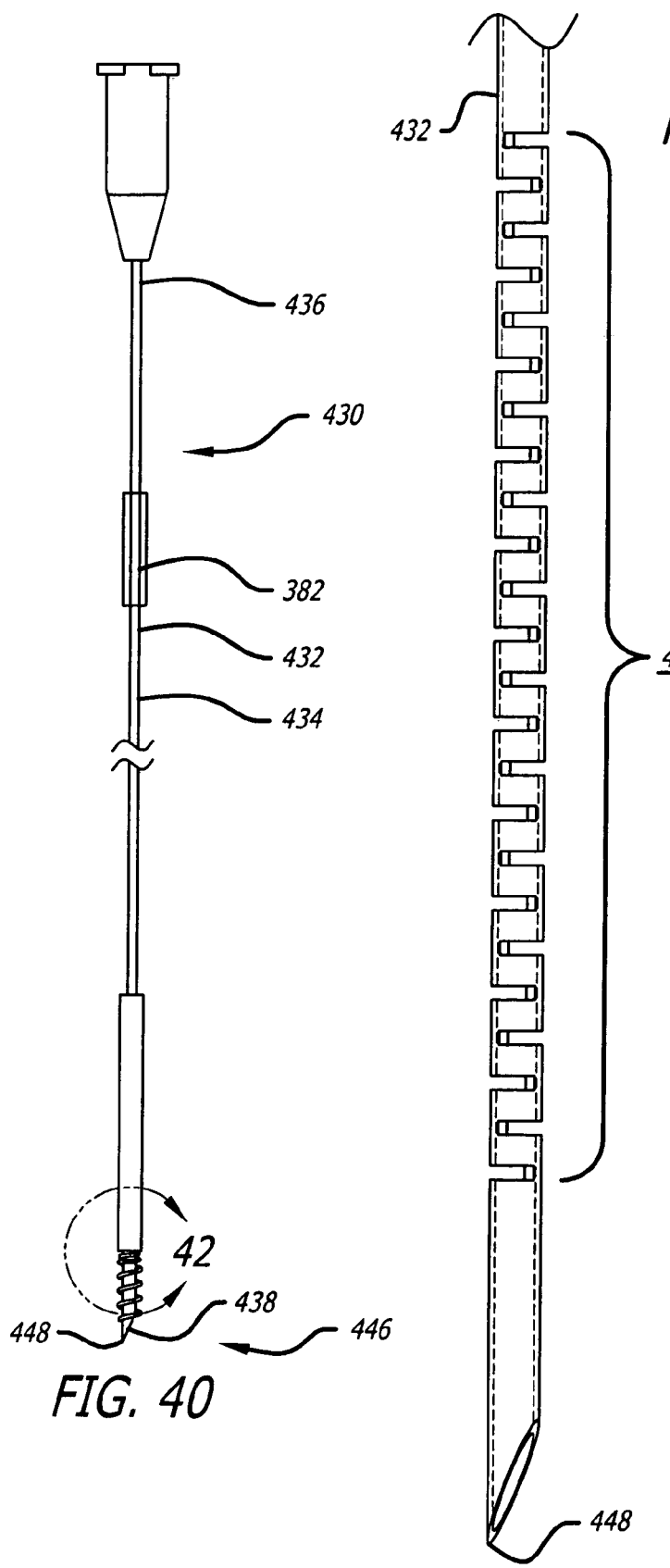
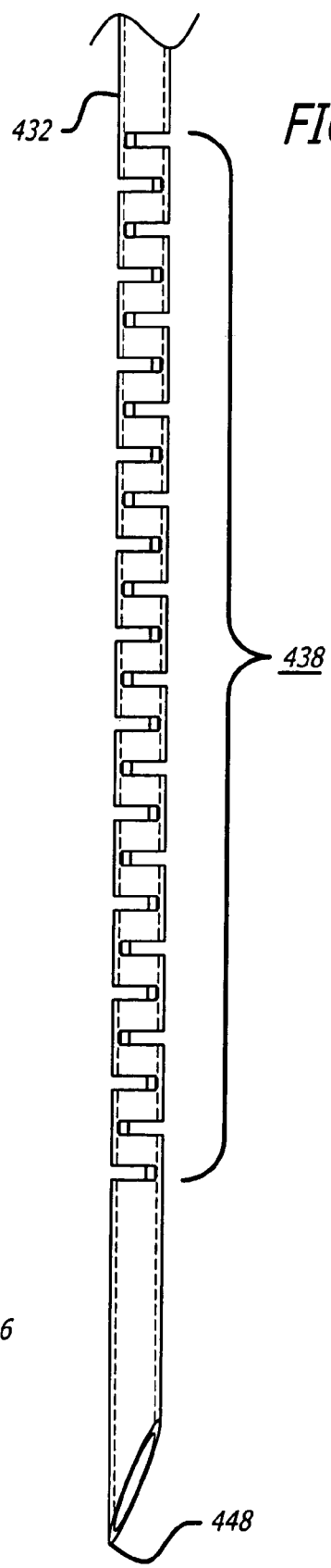
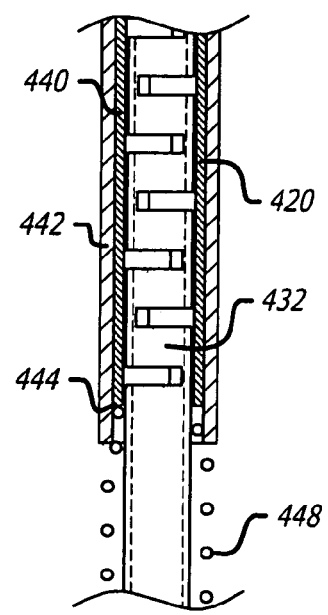
FIG. 40
FIG. 41
FIG. 42

TRANSMEMBRANE ACCESS SYSTEMS AND METHODS

BACKGROUND

Access to the left side of the heart plays an important role in the diagnosis and treatment of cardiovascular disease. Invasive cardiologists commonly perform a left heart catheterization for angiographic evaluation or transcatheter intervention of cardiac or coronary artery disease. In a left heart catheterization, the operator achieves vascular access through a femoral artery and passes a catheter in a retrograde direction until the catheter tip reaches the coronary artery ostia or crosses the aortic valve and into the left ventricle. From a catheter positioned in the left ventricle, an operator can measure left ventricular systolic and end-diastolic pressures and evaluate aortic valve disease. Ventriculography, where contrast is injected into the left ventricle, may be performed to evaluate left ventricular function. Alternative insertion sites, such as the brachial or radial artery, are used sometimes when femoral artery access is contraindicated due to iliofemoral atherosclerosis, but manipulation of the catheter can be more difficult from these other insertion sites.

Although left heart catheterization can be a fast and relatively safe procedure for access to the coronary arteries and the left ventricle, its usefulness for accessing structures beyond the left ventricle, namely the left atrium and the pulmonary veins, is limited by the tortuous path required to access these structures from the left ventricle via the mitral valve. For example, electrophysiologic procedures requiring access to the left atrium or pulmonary veins, performance of balloon mitral valve commissurotomy, and left ventricular access across an aortic prosthetic disc valve can be difficult, and sometimes unfeasible, through traditional left heart catheterization techniques.

Transseptal cardiac catheterization is another commonly employed percutaneous procedure for gaining access to the left side of the heart from the right side of the heart. Access occurs by transiting across the fibro-muscular tissue of the intra-atrial septum from the right atrium and into the left atrium. From the left atrium, other adjoining structures may also be accessed, including the left atrial appendage, the mitral valve, left ventricle and the pulmonary veins.

Transseptal cardiac catheterization has been performed in tens of thousands of patients around the world, and is used for both diagnostic and therapeutic purposes. Diagnostically, operators utilize transseptal catheterization to carry out electrophysiologic procedures requiring access to the pulmonary veins and also to do left heart catheterizations where a diseased aortic valve or an aortic disc prosthetic valve prohibits retrograde left ventricular catheterization across the valve. Therapeutically, operators employ transseptal cardiac catheterization to perform a host of therapeutic procedures, including balloon dilatation for mitral or aortic valvuloplasty and radiofrequency ablation of arrhythmias originating from the left side of the heart. Transseptal cardiac catheterization is also used to implant newer medical devices, including occlusion devices in the left atrial appendage for stroke prevention and heart monitoring devices for the treatment of cardiovascular disease.

The vast majority of transseptal procedures is performed via a femoral vein access site, using special set of devices, called a Brockenbrough needle and catheter/dilator, designed for this approach. In this standard approach the Brockenbrough catheter/dilator, with the hollow Brockenbrough needle within, is advanced from a femoral vein, through the inferior vena cava, through the right atrium and into the superior vena cava. The distal end is then pulled back to the right atrium and rotated until it points at the foramen ovale of the atrial septum. The Brockenbrough needle has a gentle bend that facilitates guiding the system from the vena cava into and through the right atrium, to the intra-atrial septum. The right atrial surface of the septum faces slightly downward, toward the inferior vena cava, so that the natural path of the Brockenbrough needle/catheter brings it to the atrial surface at nearly a right angle of incidence. After verifying the location of the catheter tip at the septal surface by fluoroscopy and/or ultrasound imaging, the operator can firmly but gradually advance the needle within the catheter until its tip penetrates the septum. Contrast material is then injected through the lumen of the Brockenbrough needle and observed fluoroscopically to verify placement of the tip in the left atrium. Once this placement is verified, the catheter/dilator may be advanced through the septum into the left atrium, the Brockenbrough needle is removed and a guide wire can be placed into the left atrium through the dilator lumen. At this point, access to the left atrium has been established and the Brockenbrough needle can be removed, allowing introduction of other devices either over the guide wire or through a Mullins sheath placed over the dilator, or both, as is well known to those skilled in the art.

Transseptal cardiac catheterization using the standard technique described above is generally successful and safe when performed by skilled individuals such as invasive cardiologists, interventional cardiologists, and electrophysiologists with appropriate training and experience. Lack of success may be attributable to anatomic variations, especially with respect to the size, location and orientation of the pertinent cardiovascular structures and imaging-related anatomic landmarks. Another reason for failure may be the relatively fixed dimensions and curvatures of currently available transseptal catheterization equipment. One major risk of existing transseptal catheterization techniques lies in the inadvertent puncture of atrial structures, such as the atrial free wall or the coronary sinus, or entry into the aortic root or pulmonary artery. In some cases, these punctures or perforations can lead to bleeding around the heart resulting in impaired cardiac function known as cardiac tamponade, which if not promptly recognized and treated, may be fatal. As such, surgical repair of such a cardiac perforation is sometimes required.

One problem with the standard transseptal needle/catheter system is that once an inadvertent puncture has occurred, it may be difficult to realize what structure has been compromised because contrast injection through the needle is limited by the small bore lumen thereof. Thus, visualization of the structure entered may be inadequate and non-diagnostic. Also, the tip of the catheter dilator of existing devices may cross the puncture site which has the effect of further enlarging the puncture hole.

Other than minor refinements in technique and equipment, the standard transseptal catheterization procedure has remained relatively constant for years. Even so, the technique has several recognized limitations that diminish the efficacy and safety of this well-established procedure. Thus, there remains a need for an alternative system that effectively and safely provides access to the left atrium, or other desired site in the body.

As noted above, standard transseptal cardiac catheterization is performed via the inferior vena cava approach from an access site in a femoral vein. In some situations it is clinically desirable to perform transseptal cardiac catheterization via the superior vena cava from an access site in a vein in the neck or shoulder area, such as a jugular or subclavian vein. The superior vena cava approach is more problematic than the standard inferior vena cava approach because of the downward anatomical orientation of the intra-atrial septum, mentioned above: the Brockenbrough needle must make more than a 90° bend to engage the atrial septum at a right angle of incidence, which makes it difficult to exert a sufficient force along the axis of the needle to penetrate the septum. In fact, it is in general problematic to exert an axial force around a bend in a flexible wire, rod, needle, or other elongated member, because the axial force tends to bend or flex the device rather than simply translate it axially. Thus, there is a need for improved apparatus and methods for performing procedures requiring an axial force, such as punctures, when a bend in the flexible member transmitting the force is unavoidable. Another problem not infrequently encountered with conventional transseptal catheterization is that advancement of a Brockenbrough needle against the septum can cause substantial displacement or tenting of the septum from right to left prior to puncture. Sudden penetration can result in the needle injuring other structures in the left atrium. Two approaches to these needs are addressed in this invention: reduction or elimination of the force required to perform the procedure, such as a transseptal puncture; and provision of a stabilizing apparatus for transmitting an axial force around a bend.

SUMMARY

One embodiment is directed to a transmembrane access system having a stabilizer sheath with a tubular configuration and an inner lumen extending therein and having a side port disposed on a distal section of the sheath and in communication with the inner lumen. A tubular guide catheter having a shaped distal section that has a curved configuration in a relaxed state and an outer surface which is configured to move axially within a portion of the inner lumen of the stabilizer sheath that extends from the proximal end of the stabilizer sheath to the side port. A tissue penetration member is disposed within a distal end of the guiding catheter and is axially extendable from the distal end of the guiding catheter for membrane penetration. In one particular embodiment, the tissue penetration member is configured to penetrate tissue upon rotation and the system further includes an elongate torqueable shaft coupled to the tissue penetration member.

Another embodiment of a transmembrane access system includes a tubular guide catheter having a shaped distal section that has a curved configuration in a relaxed state. A tissue penetration member configured to penetrate tissue on rotation includes a helical tissue penetration member. The tissue penetration member is configured to move axially within an inner lumen of the tubular guide catheter and is axially extendable from the guide catheter for membrane penetration. An activation modulator is coupled to the tissue penetration member by a torqueable shaft and is configured to axially advance and rotate the torqueable shaft upon activation of the activation modulator.

One embodiment of a method of use of a transmembrane access system includes a method of accessing the left atrium of a patient's heart from the right atrium of the patient's heart wherein a transmembrane access system is provided. The transmembrane access system includes a stabilizer sheath having a tubular configuration with an inner lumen extending therein and a side port disposed on a distal section of the sheath in communication with the inner lumen. The system also includes a tubular guide catheter having a shaped distal section that has a curved configuration in a relaxed state and an outer surface which is configured to move axially within a portion of the inner lumen of the stabilizer sheath that extends from the proximal end of the stabilizer sheath to the side port. A tissue penetration member is disposed within a distal end of the guiding catheter and is axially extendable from the distal end of the guiding catheter for membrane penetration.

Once the transmembrane access system has been provided, the stabilizer sheath is advanced over a guidewire from the vascular access site in a subclavian or jugular vein through superior vena cava of the patient and positioned with the distal end of the stabilizer sheath within the inferior vena cava with the side port of the stabilizer sheath within the right atrium facing the intra-atrial septum of the patient's heart. The guidewire is removed and the distal end of the guide catheter is advanced through the inner lumen of the stabilizer sheath until the distal end of the guide catheter exits the side port of the stabilizer sheath and is positioned adjacent target tissue of a desired site of the septum of the patient's heart. The tissue penetration member is advanced from the distal end of the guide catheter and activated so as to penetrate the target tissue. For some embodiments, the tissue penetration member is activated by rotation of the tissue penetration member. The tissue penetration member is then advanced distally through the septum.

Another embodiment of using a transmembrane access system includes a method of accessing a second side of a tissue membrane from a first side of a tissue membrane wherein a transmembrane access system is provided. The transmembrane access system includes a guide catheter with a shaped distal section that has a curved configuration in a relaxed state. The system also includes a tissue penetration member which is disposed within a distal end of the guide catheter and which is axially extendable from the distal end of the guide catheter for membrane penetration. The tissue penetration member is configured to penetrate tissue upon rotation and has a guidewire lumen disposed therein. The distal end of the guide catheter is positioned until the distal end of the guide catheter is adjacent to a desired site on the first side of the tissue membrane.

The tissue penetration member is advanced distally from the guide catheter until the distal end of the tissue penetration member is in contact with the tissue membrane. The tissue penetration member is then rotated and advanced distally through the tissue membrane. Contrast material may be injected through the guidewire lumen of the penetrating member while observing fluoroscopically to verify that the tissue penetration member has entered the desired distal chamber. Alternatively, pressure can be monitored through the guidewire lumen to verify that the tissue penetration member has entered the desired distal chamber, as is well known to those skilled in the art. It is also well known to both inject contrast under fluoroscopic observation and to monitor pressure through the same lumen to verify positioning of the tissue penetration member. Finally, a guidewire is advanced through the guidewire lumen of the tissue penetration member until a distal end of the guidewire is disposed on the second side of the tissue membrane.

These and other advantages of embodiments will become more apparent from the following detailed description when taken in conjunction with the accompanying exemplary drawings.

BRIEF DESCRIPTION OF THE DRAWINGS

FIG. 3 is an enlarged view in longitudinal section of the tissue penetration member and attachment of the tissue penetration member to the torqueable shaft.

FIG. 3A is a transverse cross sectional view of the joint between the tissue penetration member and torqueable shaft indicated by lines 3A-3A in FIG. 3.

FIG. 3B is an elevational view of the tissue penetration member and torqueable shaft of the entire elongate tissue penetration device.

FIGS. 3C and 3D illustrate transverse cross sectional views of the elongate tissue penetration device taken along lines 3C-3C and 3D-3D of FIG. 3B, respectively.

FIG. 6 is an elevational view of the stabilizer sheath of FIG. 5 shown with the curved distal section lying in the plane of the page and with the proximal adapter not shown attached to the Luer connector fitting.

FIG. 7 is an enlarged transverse cross sectional view of the stabilizer sheath taken at the side port along lines 7-7 of FIG. 6.

FIG. 7A is a transverse cross sectional view of the stabilizer sheath taken along lines 7A-7A of FIG. 7.

FIG. 14 illustrates an embodiment of an obturator sheath configured to be disposed within the inner lumen of the stabilizer sheath and block the side port of the stabilizer sheath to prevent damage to tissue adjacent the stabilizer sheath during insertion thereof.

FIG. 15 illustrates an enlarged view in longitudinal section of the obturator disposed within the side port of the stabilizer sheath and having a guidewire disposed within the inner lumen of the obturator sheath.

FIG. 16 is a transverse cross sectional view of the stabilizer sheath, obturator sheath and guidewire taken along lines 16-16 of FIG. 15.

FIG. 17 is an elevational view in longitudinal section of the distal end of the obturator sheath illustrating the tapered configuration of the distal end of the obturator sheath and showing the guidewire disposed within and extending from the inner lumen of the obturator sheath.

FIG. 17A illustrates an enlarged view in section of an alternative embodiment of a side port configuration of an embodiment of a stabilizer sheath wherein the guidewire extending through the inner lumen of the stabilizer sheath embodiment is maintained in a concentric arrangement with the longitudinal axis of the stabilizer sheath by a sleeve portion that is also shaped within the side port to act as a deflective surface.

FIG. 19 shows an enlarged elevational view of the side port section of the stabilizer sheath after removal of the obturator sheath with the distal end of the guide catheter and the distal end of the tissue penetration device, disposed within the distal end of the guidewire, being advanced distally through the inner lumen of the stabilizer sheath to the side port.

FIG. 40 is an elevational view, partially broken away, of yet another alternative embodiment of a tissue penetration device.

FIG. 41 illustrates a distal portion of a tubular needle of the tissue penetration device of FIG. 40 which has a series of alternating partial transverse cuts in the tubular member to enhance the flexibility of the distal portion of the tubular needle.

FIG. 42 is an enlarged view in longitudinal section of the tissue penetration device of FIG. 37 indicated by the encircled portion 42-42 in FIG. 40.

DETAILED DESCRIPTION

Embodiments are directed to systems and methods for accessing a second side of a tissue membrane from a first side of a tissue membrane. In more specific embodiments, devices and methods for accessing the left atrium of a patient's heart from the right atrium of a patient's heart are disclosed. Indications for such access devices and methods can include the placement of cardiac monitoring devices, transponders or leads for measuring intracardiac pressures, temperatures, electrical conduction patterns and voltages and the like. The deployment of cardiac pacemaker leads can also be facilitated with such access devices and methods. Such access can also be useful in order to facilitate the placement of mitral valve repair devices and prosthetics.

Figure 1:
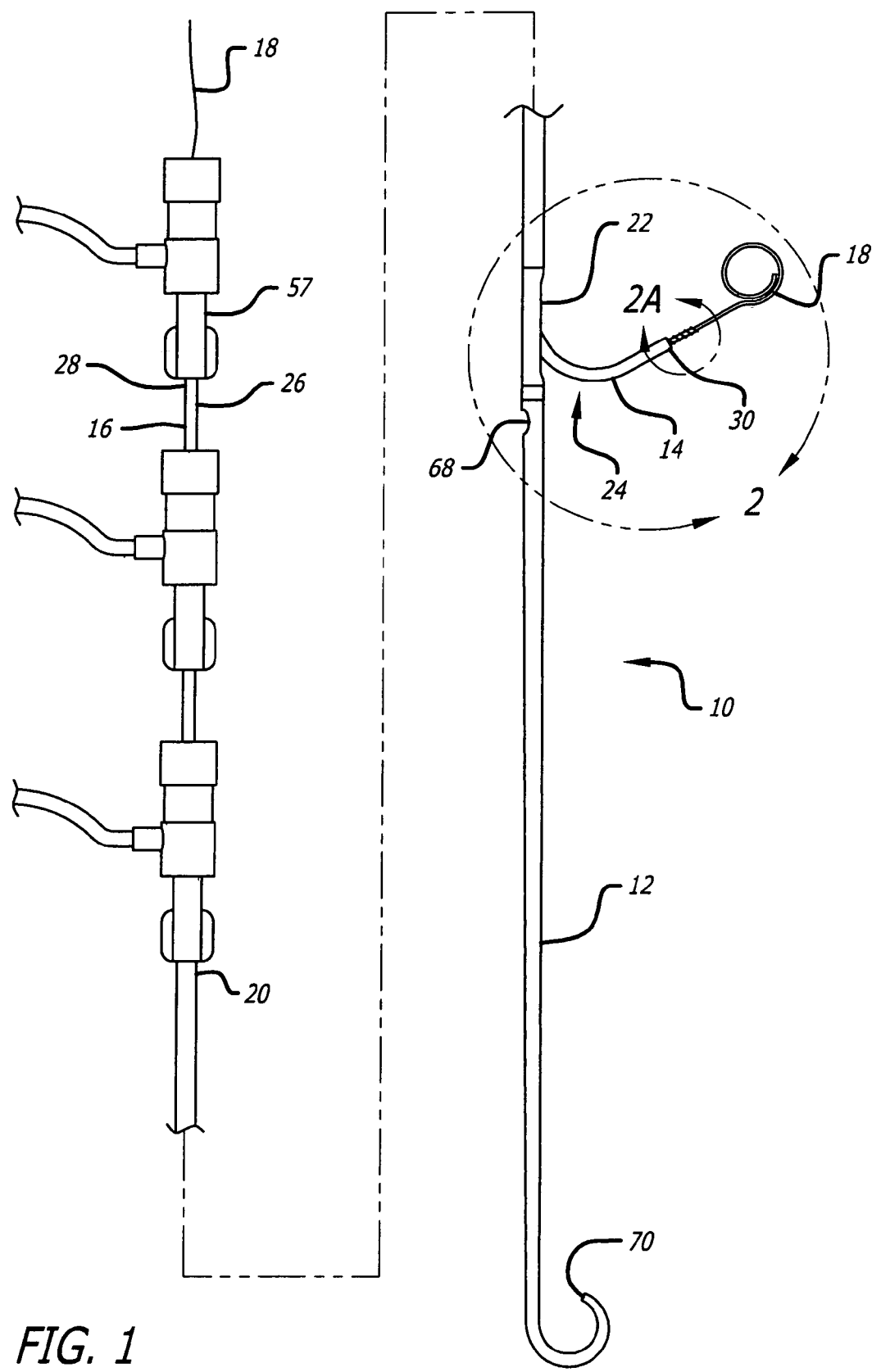
FIG. 1 is an elevational view of an embodiment of a transmembrane access system.

FIG. 1 illustrates an embodiment of a transmembrane access system 10. The system 10 shown in FIG. 1 includes a stabilizer sheath 12, a guide catheter 14, an elongate tissue penetration device 16 and a guidewire 18 disposed within an inner lumen of the elongate tissue penetration device 16. The stabilizer sheath 12 has a tubular configuration with an inner lumen 13 extending from a proximal end 20 of the stabilizer sheath 12 to a side port 22 disposed in the sheath 12. In one embodiment, the inner lumen 13 extends to the distal port 70 of the stabilizer sheath 12, and is open to one or more side ports 22 at one or more locations between the proximal and distal ends. The guide catheter 14 has a tubular configuration and is configured with an outer surface profile which allows the guide catheter 14 to be moved axially within the inner lumen of the stabilizer sheath 12. The guide catheter 14 has a shaped distal section 24 with a curved configuration in a relaxed state which can be straightened and advanced through the inner lumen of the stabilizer sheath 12 until it exits the side port 22 of the stabilizer sheath 12 as shown in more detail in FIG. 2.

The elongate tissue penetration device 16 includes a tubular flexible, torqueable shaft 26 having a proximal end 28, shown in FIG. 1, and a distal end 30. The distal end 30 of the torqueable shaft 26 is secured to a tissue penetration member 32, shown in FIG. 2A, which is configured to penetrate tissue upon activation by rotation of the tissue penetration member 32. The tissue penetration member 32 has a tubular needle 34 with a proximal end 36, a sharpened distal end 38 and an inner lumen 40 that extends longitudinally through the tubular needle 34. A helical tissue penetration member 42 has a proximal end 44 and a sharpened distal end 46 and is disposed about the tubular needle 34. The helical tissue penetration member 42 has an inner diameter which is larger than an outer diameter of the tubular needle 34 so as to leave a gap between the tubular needle 34 and the helical tissue penetration member 42 for the portion of the helical tissue penetration 42 that extends distally from the distal end 30 of the torqueable shaft 26. Referring to FIG. 3, a proximal portion 48 of a coil of the helical tissue penetration member 42 is secured to a distal portion 50 of the inner lumen of the tubular torqueable shaft 26 and a proximal portion 52 of the tubular needle 34 is secured to the proximal portion 48 of the coil of the helical tissue penetration member 42. A conical ramp 54 may be disposed at the proximal end 56 of the tubular needle 34 in order to form a smooth transition from the inner lumen 58 of the tubular torqueable shaft 26 to the inner lumen 40 of the tubular needle 34 which facilitates guidewire movement therethrough. The proximal end 56 of the tubular needle 34 may also have a tapered section 55 formed or machined into the inner surface of the tubular needle 34.

Figure 2:
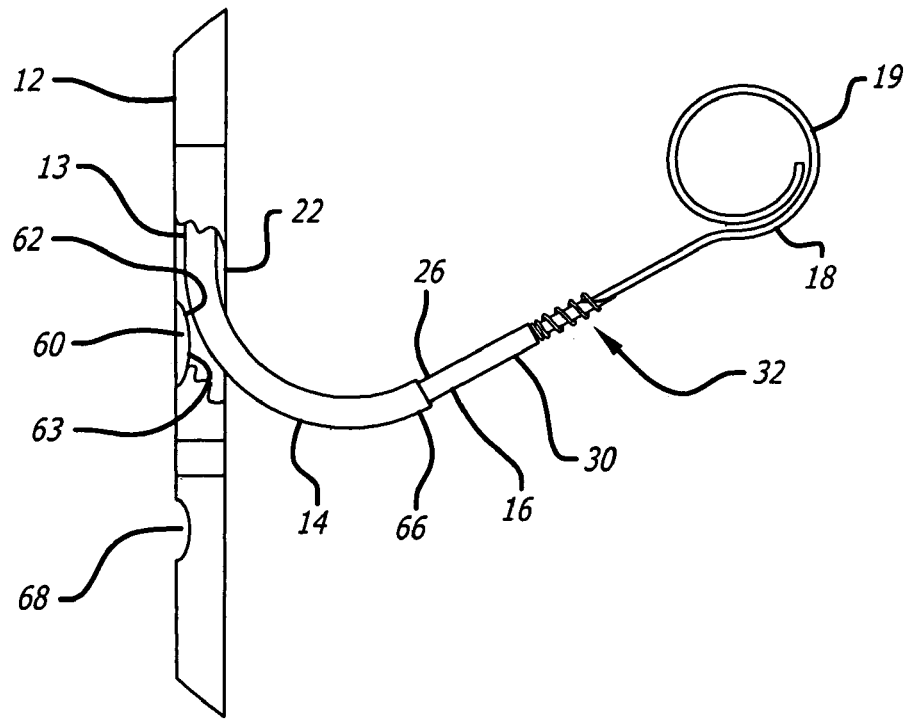
FIG. 2 is an enlarged view in partial section of the side port portion of the transmembrane access system of FIG. 1 indicated by the encircled portion 2-2 of FIG. 1 and showing a distal portion of the guide catheter and tissue penetration member secured to a distal end of the torqueable shaft to form the elongate tissue penetration device.
Figure 2A:
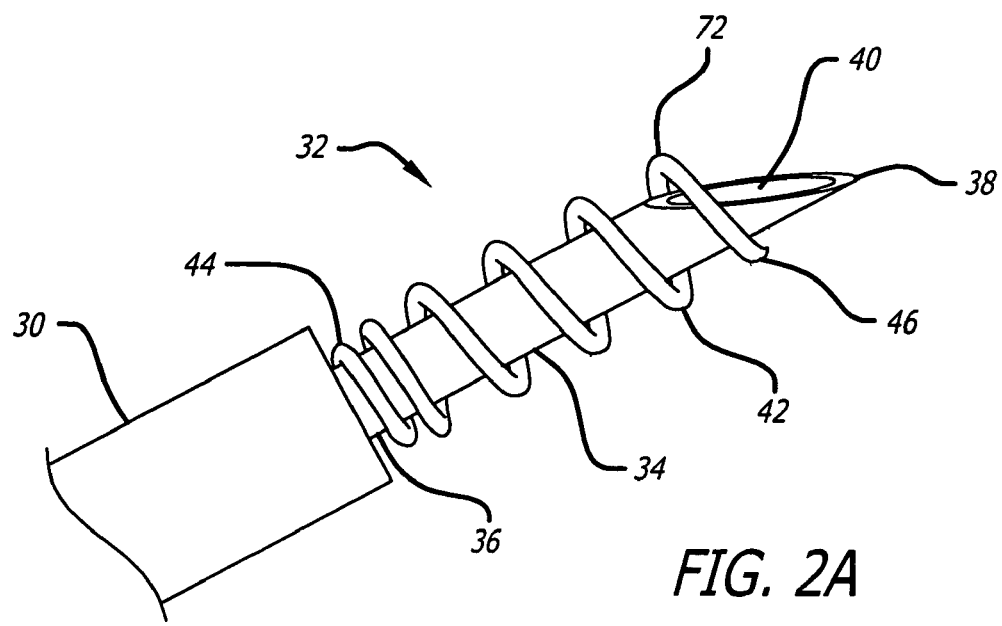
FIG. 2A is an enlarged view of the tissue penetration member secured to the torqueable shaft, indicated by the encircled portion 2A-2A in FIG. 2.

Referring to FIG. 2, an abutment 60 having a radially deflective surface 62 is disposed within the inner lumen 13 of the stabilizer sheath 12 opposite the side port 22 of the sheath 12. In the embodiment shown, the apex 63 of the abutment 60 is disposed towards the distal end of the side port 22 which disposes the deflective surface 62 in a position which is longitudinally centered in the side port 22. This configuration allows for reliable egress of the distal end 66 of the guide catheter 14 from the side port 22 after lateral deflection of the guide catheter 14 by the deflective surface 62. The deflective surface 62 of the abutment 60 serves to deflect the distal end 66 of the guide catheter 14 from a nominal axial path and out of the side port 22 during advancement of the guide catheter 14 through the inner lumen 13 of the stabilizer sheath 12. The abutment 60 may be a fixed mass of material or may be adjustable in size and configuration. In one embodiment the abutment 60 is inflatable and has an inflation lumen extending proximally through the stabilizer sheath 12 from the inflatable abutment to the proximal end 20 of the stabilizer sheath 12. An optional guidewire exit port 68 may be disposed in the wall of the stabilizer sheath 12 distal of the side port 22 that is in fluid communication with a distal guidewire port 70 of the stabilizer sheath 12. Such a configuration allows the stabilizer sheath 12 to be advanced into position over a guidewire (not shown) with the guide catheter 14 and elongate tissue penetration device 16 disposed in the inner lumen 13 of the stabilizer sheath 12. A standard guidewire may also be disposed in the distal guidewire port 70 of the stabilizer sheath 12 and extend proximally in the inner lumen 13 of the stabilizer sheath 12 to the proximal end 20 of the sheath 12. Guidewire 18 that may be used in conjunction with the tissue penetration device 16 may be an Inoue wire, manufactured by TORAY Company, of JAPAN. This type of guidewire 18, such as the Inoue CMS-1 guidewire, may have a length of about 140 cm to about 260 cm, more specifically, about 160 cm to about 200 cm. The guidewire 18 may have a nominal transverse outer dimension of about 0.6 mm to about 0.8 mm. The distal section 19 of this guidewire 18 embodiment may be configured to be self coiling which produces an anchoring structure.

The elongate tissue penetration device 16, as shown in more detail in FIGS. 3-3D, includes the tubular torqueable shaft 26 secured to the tissue penetration member 32 at a distal end of the tubular torqueable shaft 26 and a Luer fitting 57 at the proximal end 28 of the shaft 26. FIGS. 3 and 3A illustrate an enlarged view in section of the junction between the tissue penetration member 32 and the tubular torqueable shaft 26. As shown, the proximal portion 48 of the coil of the helical tissue penetration member 42 is secured to the distal portion 50 of the inner lumen 58 of the tubular torqueable shaft 26 by an adhesive. Adhesives such as epoxy, UV epoxy or polyurethane may be used. Other suitable methods of joining the helical tissue penetration member 42 to the tubular torqueable shaft 26 may include soldering, welding or the like. The proximal portion 52 of the tubular needle 34 is secured to the proximal portion 48 of the helical tissue penetration member 42 in a substantially concentric arrangement also by an adhesive that may be the same as or similar to those discussed above. The conical ramp 54 is disposed at the proximal end 56 of the tubular needle 34 in order to form a smooth transition from the inner lumen 58 of the tubular torqueable shaft 26 to the inner lumen 40 of the tubular needle 34 and may be formed of a polymer or epoxy material. The distal end 46 of the helical tissue penetration member 42 has a sharpened tip 38 in order to facilitate tissue penetration upon rotation and advancement of the tissue penetration member 32.

The outer transverse dimension or diameter of the helical tissue penetration member 42 may be the same as or similar to an outer transverse dimension or diameter of the tubular torqueable shaft 26. Alternatively, the outer transverse dimension or diameter of the helical tissue penetration member 42 may also be greater than the nominal outer transverse dimension of the tubular torqueable shaft 26. The outer transverse dimension of an embodiment of the helical tissue penetration member 42 may also taper distally to a larger or smaller transverse dimension.

The helical tissue penetration member 42 can have an exposed length distally beyond the distal end 30 of the torqueable shaft 26 of about 4 mm to about 15 mm. The inner transverse diameter of the coil structure of the helical tissue penetration member 42 can be from about 0.5 mm to about 2.5 mm. The pitch of the coil structure may be from about 0.3 mm to about 1.5 mm of separation between axially adjacent coil elements of the helical tissue penetration member 42. In addition, helical tissue penetration member embodiments may include coil structures having multiple elongate wire coil elements 72 that can be wound together. The elongate wire element 72 may have an outer transverse dimension or diameter of about 0.02 mm to about 0.4 mm. The helical tissue penetration member can be made of a high strength material such as stainless steel, nickel titanium alloy, MP35N, Elgiloy or the like. The elongate coiled element 72 may also be formed of a composite of two or more materials or alloys. For example, one embodiment of the elongate coiled element 72 is constructed of drawn filled tubing that has about 70 percent to about 80 percent stainless steel on an outer tubular portion and the remainder a tantalum alloy in the inner portion of the element. Such a composition provides high strength for the helical tissue penetration member 42 is compatible for welding or soldering as the outer layer of material may be the same or similar to the material of the braid of the torqueable shaft 26 or the tubular needle 34. Such a drawn filled configuration also provides enhanced radiopacity for imaging during use of the tissue penetration device 16.

The tubular needle 34 of the tissue penetration member 34 may be made from tubular metallic material, such as stainless steel hypodermic needle material. The outer transverse dimension of an embodiment of the tubular needle 34 may be from about 0.25 mm to about 1.5 mm and the inner transverse dimension or diameter of the inner lumen 40 of the tubular needle 34 may be from about 0.2 mm to about 1.2 mm. The wall thickness of the tubular needle 34 may be from about 0.05 mm to about 0.3 mm. The tubular needle 34 may be made from other high strength materials such as stainless steel, nickel titanium alloy, MP35N, monel or the like.

The tubular torqueable shaft 26 has a distal section 74 and a proximal section 76 as shown in FIG. 3B. The proximal section 76 of the shaft 26 has a tubular polymer layer 78 disposed about a high strength tubular member 80. The tubular polymer layer 78 may be made from materials such as Pebax, polyurethane, or the like. The material of the tubular polymer layer 78 may have a hardness of about 25 D shore hardness to about 75 D shore hardness. The high strength tubular member 80 may be made from materials such as stainless steel, nickel titanium alloy, MP35N, monel or the like. The distal section 74 of the tubular torqueable shaft 26 may be constructed from a tubular polymer 82 similar to that of the proximal section 76 which is reinforced by a braid 84 of high strength material that provides torqueability to the distal section 74 while maintaining the flexibility of the distal section 74. The reinforcing braid 84 may be disposed on an inside surface 86 or outside surface 88 of the tubular polymer material 82 of the distal section 74. Alternatively, the reinforcing braid 84 may also be embedded in the tubular polymer material 82 of the distal section 74 as shown in FIG. 3D. The elongate tissue penetration device 16 may have an overall length of about 3 mm to about 20 mm, more specifically, about 4 mm to about 12 mm. Alternative embodiments of the torqueable shaft 26 can be a single composite extrusion of plastic and high strength braid with a varying durometers polymer along its length so that the torqueable shaft 26 is flexible at the distal end and rigid at the proximal end of the torqueable shaft 26.

Figure 4:
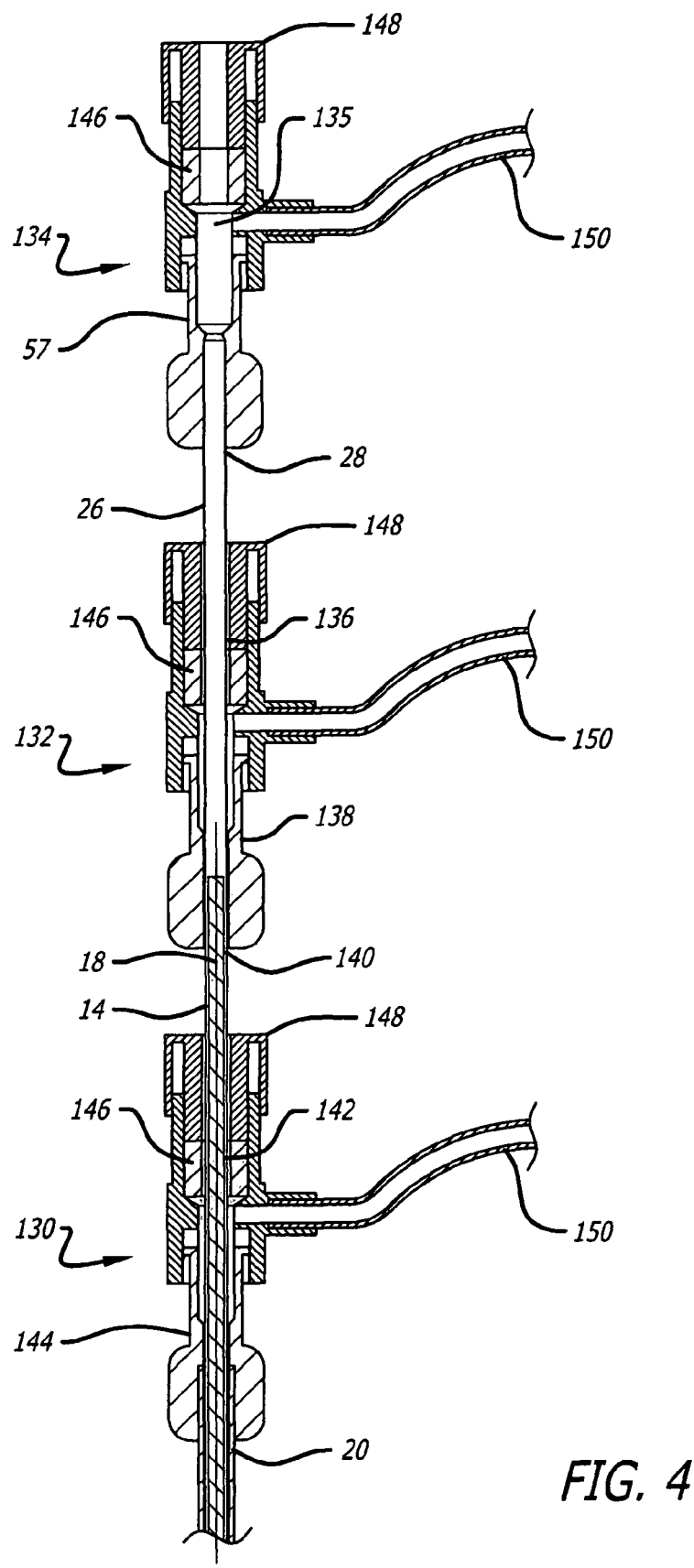
FIG. 4 is an enlarged view in longitudinal section of the proximal adapters of the proximal portion of the transmembrane access system of FIG. 1.
Figure 5:
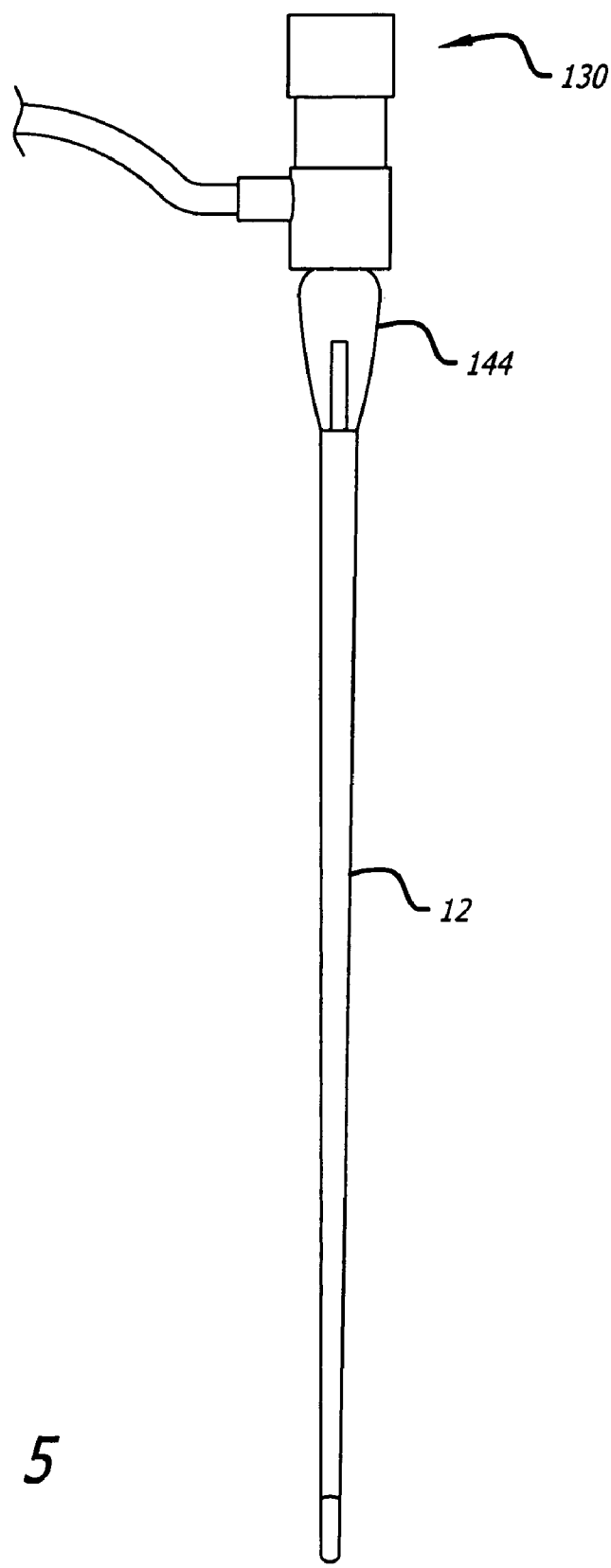
FIG. 5 is an elevational view of the stabilizer sheath of the transmembrane access system of FIG. 1 with the curved distal portion of the sheath lying in a plane which is orthogonal to the page.

FIG. 4 is an enlarged view in longitudinal section of the proximal adapters 130, 132 and 134 of the proximal portion of the transmembrane access system 10 shown in FIG. 1. The guidewire 18 is not shown for clarity of illustration. Proximal adapter 134, having inner lumen 135, is secured to the Luer fitting 57 on the proximal end 28 of the tubular torqueable shaft 26 of the elongate tissue penetration device 16. The elongate tissue penetration device 16 passes through an inner lumen 136 of proximal adapter 132 which is secured to a Luer fitting 138 secured to a proximal end 140 of the guide catheter 14. The guide catheter 14 and elongate tissue penetration device 16 are disposed within an inner lumen 142 of proximal adapter 130 which is secured to a Luer fitting 144 secured to the proximal end 20 of the stabilizer sheath 12. The proximal adapters 130, 132 and 134 all have inner lumens 135, 136 and 142 which allow for passage of appropriately sized devices while maintaining a seal between the devices and the inner lumens 135, 136 and 142. Each proximal adapter includes a resilient annular seal 146 that may be compressed by a threaded compression cap 148 so as to constrict the seal and form a seal around an outside surface of a catheter or other device disposed within an inner lumen of the seals 146. Each proximal adapter 130, 132 and 134 is also configured with a side port 150 in fluid communication with the respective inner lumens 135, 136 and 142 of the proximal adapters to allow for aspiration and flushing of the inner lumen, injection of contrast material, measurement of fluid pressure and the like. A proximal adapter embodiment suitable for use with embodiments 130, 132 and 134 of the system 10 can include the Toughy Borst made by Martek Company or commercially available hemostasis valves, including rotating hemostasis valves.

FIGS. 5-11 illustrate the stabilizer sheath 12 in more detail. The stabilizer sheath 12 has a substantially tubular configuration with a distal section 152 that tapers to a reduced transverse dimension or diameter and includes a pigtail or curled section 154 at the distal end 156 of the sheath 12 to avoid udesireable entry into small vessels and reduce vascular trauma. The side port 22, detailed in FIGS. 7 and 8, includes the abutment 60 having the radially deflective surface 62 disposed within the inner lumen 13 of the stabilizer sheath 12 opposite the side port 22 of the sheath 12. The deflective surface 62 forms an approximate angle 158 with the nominal longitudinal axis 160 of the side port section 162 of the stabilizer sheath 12 and extends radially inward from the nominal surface 164 of the inner lumen 13 of the stabilizer sheath 12. The deflective surface 62 of the abutment 60 serves to deflect the distal end 66 of the guide catheter 14 out of the side port 22 during advancement of the guide catheter 14 through the inner lumen 13 of the stabilizer sheath 12. The optional guidewire exit port 68 may be disposed in the wall of the stabilizer sheath 12 distal of the side port 22 that is in fluid communication with a distal guidewire port 70 of the stabilizer sheath 12.

The side port 22 is configured to allow egress of the distal section 24 of the guide catheter 14 and elongate tissue penetration device 16. The side port 22 may have an axial or longitudinal length of about 10 mm to about 20 mm. The side port 22 may a width of about 1.5 mm to about 4 mm. The side port section 162 of the stabilizer sheath 12 may also include a reinforcement member 166 that strengthens the side port section 162 of the sheath 12 where material of the sheath 12 has been removed in order to create the side port 22. The reinforcement member 166 as well as the stabilizer sheath 12 optionally includes a peel away tear line 167 shown in FIGS. 7 and 7A that extends from the side port 22 of the stabilizer sheath 12 proximally to the proximal Luer fitting 144. The tear line 167 provides a fluid tight but weakened fault line that allows the stabilizer sheath to be removed from the patient's body without removal of the tissue penetration device 16 disposed within the inner lumen of the stabilizer sheath 12 when the tissue penetration device is positioned within the patient's body. The proximal adapter 130 and proximal Luer fitting 144 may also include a peel away tear line (not shown) in order to facilitate peel away removal of the stabilizer sheath 12.

Figure 8:
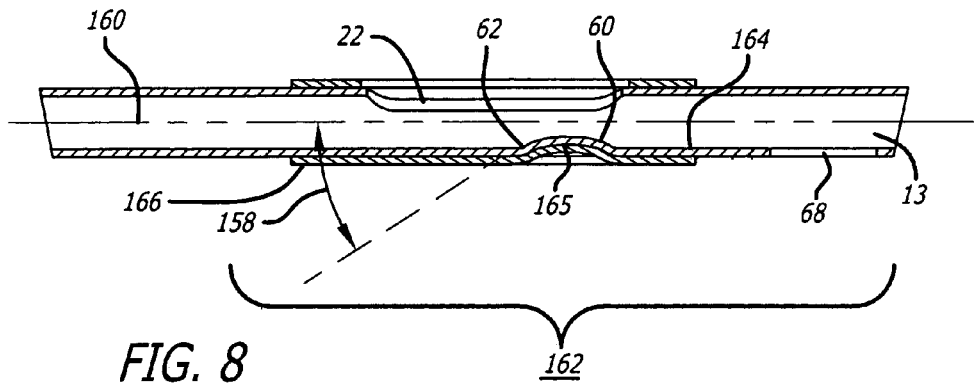
FIG. 8 is an enlarged view in longitudinal section of the side port of the stabilizer sheath indicated by the encircled portion 8-8 in FIG. 6.
Figure 8A:
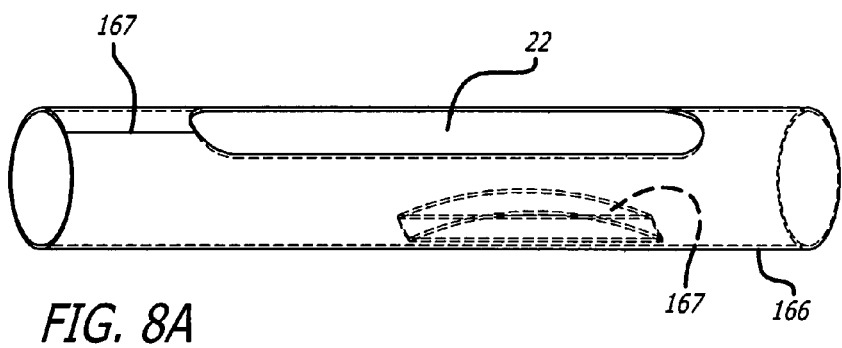
FIG. 8A is a perspective view of the reinforcement member of the side port section of the stabilizer sheath of FIG. 8.

The reinforcement member 166 may have a feature integrated within to collapse a portion of the inner lumen of the stabilizer sheath 12 and create the abutment or ramp 60 or alternatively a component, such as a dowel pin section or the like, can be trapped between the inner wall of the reinforcement member 166 and the outer wall of the stabilizer sheath 12 or an adhesive can be placed on the inner wall of the stabilizer sheath 12. The reinforcement member 166 shown in FIGS. 8 and 8A includes a deflected section 165 that displaces the stabilizer sheath wall to create the abutment 60. The reinforcement member 166 may be made from a section of high strength tubular material bonded or secured to the outer surface of the stabilizer sheath 12 that is cut to an outline that matches the side port 22 of the sheath 12. The reinforcement member 166 may have a length of about 15mm to about 30mm. The reinforcement member 166 may have a wall thickness of about 0.05mm to about 0.2mm. The reinforcement member 166 may be made from any suitable high strength material such as stainless steel, nickel titanium alloy, MP35N, Elgiloy, composites such as carbon fiber composites, or the like.

Figure 8B:
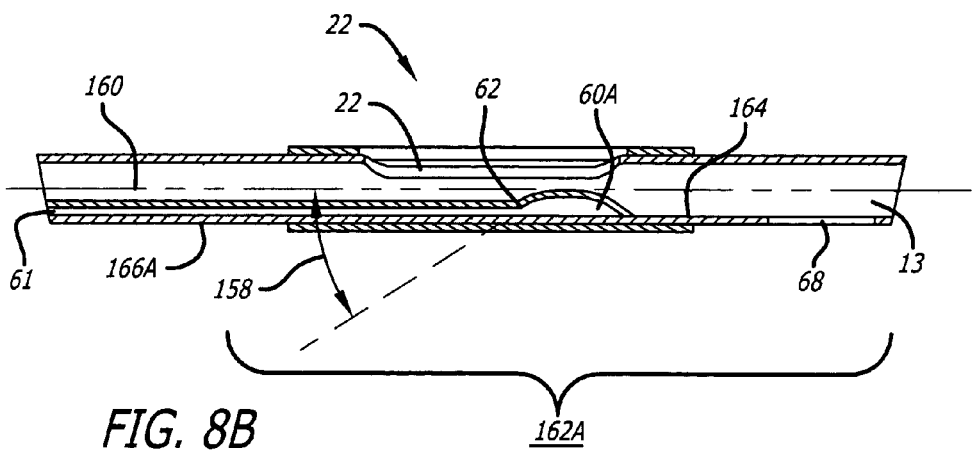
FIG. 8B illustrates the side port section of an embodiment of the stabilizer sheath having an inflatable abutment.

The abutment 60 may be a fixed mass of material or may be adjustable in size and configuration. In one embodiment, the abutment 60 is inflatable and has an inflation lumen extending proximally through the stabilizer sheath 12 from the inflatable abutment 60 to the proximal end 20 of the stabilizer sheath 12. FIG. 8B illustrates the side port section 162 of an embodiment of the stabilizer sheath 12 having an inflatable abutment 60A that may be inflated for varying sizes by injection of an inflation fluid, gas or the like through an inflation lumen 61. The inflatable abutment 60A may be made from a compliant or non-compliant material. For inflatable abutment embodiments made from compliant materials, such as elastomers, the size of the abutment 60A may be adjusted by the amount of expansion or distention of the abutment 60A which could be controlled by the pressure level of the inflation substance. The side port section 162A includes a reinforcement member 166A that does not include a deflected section 165 as shown on the reinforcement member 166 discussed above.

Figure 9:
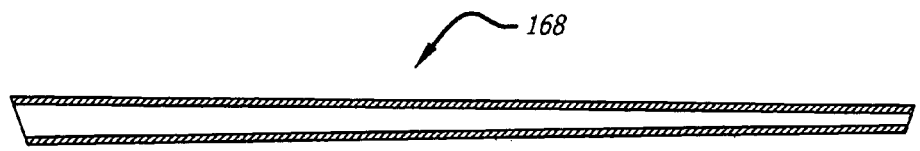
FIG. 9 is an enlarged view in longitudinal section of distal portion of the stabilizer sheath immediately distal of the side port indicated by the encircled portion 9-9 in FIG. 6 and illustrating the tapered characteristic of the distal portion of the stabilizer sheath.
Figure 11:
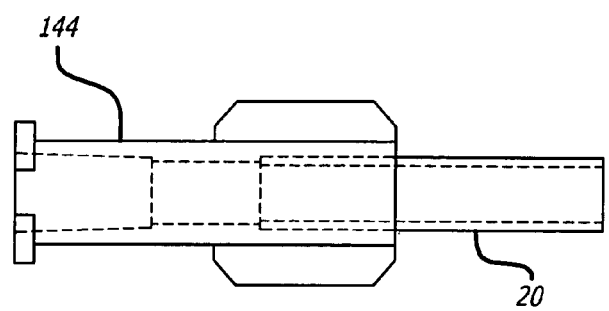
FIG. 11 is an enlarged view in longitudinal section of the proximal end portion of the stabilizer sheath indicated by the encircled portion 11-11 in FIG. 6 and illustrating the inner lumen of the stabilizer sheath and the Luer connector secured to the proximal end of the stabilizer sheath.

FIG. 9 illustrates the tapered characteristic a distal section 168 of the stabilizer sheath 12 immediately distal of the side port 22. The outer transverse dimension or diameter of the stabilizer sheath 12 may taper continuously from the side port 22 to the distal end 156 of the sheath 12. The inclusive taper angle of the sheath 12 over this distal section may be from about 0.1 degrees to about 5.0 degrees The nominal outer transverse dimension or diameter of the stabilizer sheath 12 may be from about 2.5 mm to about 6.0 mm, specifically, from about 3 mm to about 4 mm. The inner transverse dimension or diameter of the inner lumen 13 of the stabilizer sheath between the side port 22 and the Luer fitting 144, which is sized to accept the outer dimension of the guide catheter 14, may be from about 2.0 mm to about 5.0 mm. The Luer fitting 144 is secured to the proximal end 20 of the sheath by any suitable bonding method such as adhesive bonding, welding or the like. The Luer fitting 144 and joint between the Luer fitting 144 and proximal end 20 of the sheath 12 is shown in FIG. 11.

The distal end 156 of the stabilizer sheath 12 can include the curled section 154 having curvature or a "pig tail" arrangement which produces an atraumatic distal end 156 of the stabilizer sheath 12 while positioned within a patient's anatomy. The curled section 154 may have a radius of curvature of about 3 mm to about 12 mm and may have an angle of curvature 170 between a discharge axis 172 of the distal end 156 of the stabilizer sheath 12 and the nominal longitudinal axis 174 of the stabilizer sheath 12 of about 200 degrees to about 350 degrees. The inner transverse dimension of the inner lumen 13 of the sheath 12 at the distal end 156 of the sheath 12 may be from about 0.5 mm to about 1.6 mm. The overall length of the stabilizer sheath 12 may be from about 40 cm to about 100 cm. The distance from the side port 22 to the distal end 156 of the sheath 12 may be from about 30 cm to about 65 cm. The stabilizer sheath 12 may be made from any suitable flexible material which is biocompatible, such as Pebax, polyurethane, polyethylene, and the like.

Figures 12, 12A, 13:
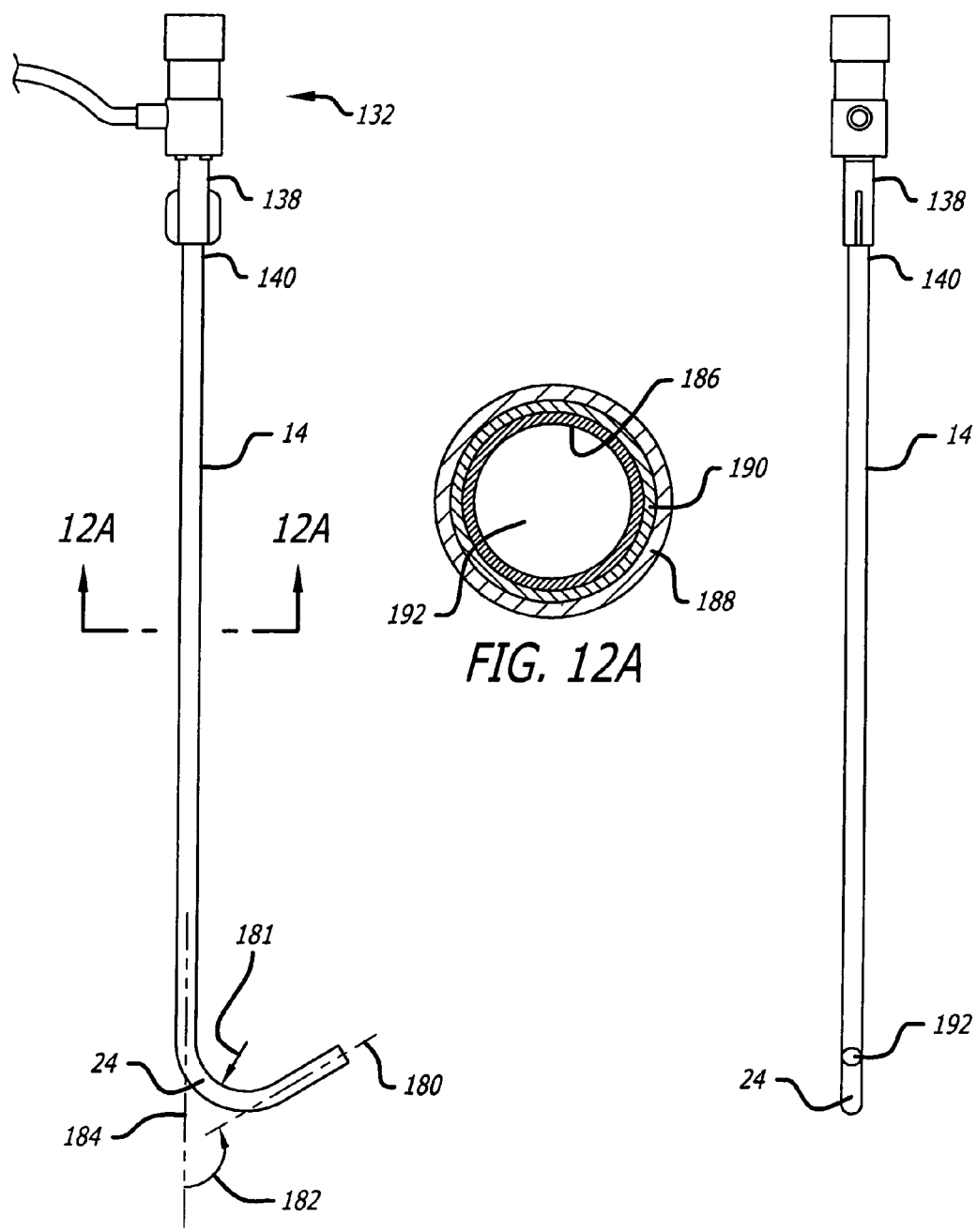
FIG. 12 illustrates the guide catheter of FIG. 1 showing the curved distal section of the guide catheter lying in the plane of the page with the guide catheter in a relaxed state.
FIG. 13 illustrates the guide catheter of FIG. 1 showing the curved distal section of the guide catheter lying in a plane that is orthogonal to the page with the guide catheter in a relaxed state.
FIG. 12A illustrates a transverse cross sectional view of the guide catheter taken along lines 12A-12A of FIG. 12 and showing the braided layer of the guide catheter.

FIGS. 12-13 illustrate the embodiment of the guide catheter 14 of FIG. 1 showing the curved distal section 24 of the guide catheter 14 while the guide catheter 14 is in a relaxed state. The guide catheter 14 has a Luer fitting 138 secured to the proximal end 140 of the guide catheter 14. The curved distal section 24 may have an inner radius of curvature 181 of about 1 cm to about 4 cm. The discharge axis 180 of the guide catheter 14 may form an angle 182 with the nominal longitudinal axis 184 of the guide catheter 14 of about 90 degrees to about 270 degrees. Although many commercially available guide catheters 14 have a soft pliable distal tip for atraumatic advancement into a patient's vasculature, this may not be desirable in some instances for use with embodiments of the access systems discussed herein. More specifically, for some procedures, it may be necessary for the distal end of the guide catheter to have sufficient structural rigidity to maintain the round transverse cross section at the distal tip of the guide catheter so that the wall of the guide catheter at the distal tip does not collapse when pressed against target tissue. Such wall collapse or deformation could cause the tissue penetration device 16 to impinge on the wall of the guide catheter which may impede progress or the procedure generally. It may be desirable for the guide catheter to have a distal tip or distal section that has a wall structure with a nominal flexibility or shore hardness that is substantially similar to or the same as the nominal flexibility or shore hardness of the shaft proximal to the distal tip or section.

The guide catheter 14 may be made from a standard guide catheter construction that includes a plurality of polymer layers 186 and 188 reinforced by a braid 190. The nominal outer transverse dimension or diameter of the guide catheter 14 may be from about 0.04 inches to about 0.10 inches. The overall length of the guide catheter 14 should be sufficiently longer than the overall length of the stabilizer sheath 12 from its proximal end to the side port 22 including the length of its proximal adapter 130 and may be from about 40 cm to about 80 cm. The inner transverse dimension of the inner lumen 192 of the guide catheter 14 may be from about 0.03 inches to about 0.09 inches. I may desirable to select the flexibility of embodiments of the guide catheter 14, and particularly the curved distal section 24 of the guide catheter 14, and the flexibility of the tissue penetration member 32 such that the tissue penetration member 32 does not substantially straighten the curved distal section 24 of the guide catheter 14 when the tissue penetration device 16 is being advanced through the guide catheter 14. Otherwise, the maneuverability of the stabilizer sheath 12 and guide catheter 14 combination could be compromised for some procedures.

Suitable commercially available guide catheters 14 with distal curves such as a "hockey stick", Amplatz type, XB type, RC type, as well as others, may be useful for procedures involving transseptal access from the right atrium of a patients heart and the left atrium of the patient's heart. Guide catheters 14 have a "torqueable" shaft that permits rotation of the shaft. Once the distal tip of the guide catheter has exited the stabilizer sheath side port and extended more or less radially away from the stabilizer sheath, rotation of the guide catheter shaft causes its distal end to swing in an arc around the axis of the stabilizer sheath, providing for lateral adjustment of the guide catheter distal tip for precise positioning with respect to the septum. The variety of distal curve shapes described above and illustrated in FIGS. 12 and 13 are curves lying in a single plane. More complex distal curve shapes involving three dimensional space may also be useful. One such example commonly used in coronary angioplasty is the XB-LAD shape where the most distal portion of the curve is bent in another plane.

FIG. 14 illustrates an embodiment of an obturator sheath 196 configured to be disposed within the inner lumen 13 of the stabilizer sheath 12 and block the side port 22 of the stabilizer sheath 12 to prevent damage to tissue adjacent the stabilizer sheath 12 and stop blood flow into the stabilizer sheath 12 during insertion of the stabilizer sheath 12 in a patient's anatomy. The obturator sheath 196 has a substantially tubular configuration with proximal end 198, a distal end 200 and an inner lumen 202 extending through the obturator sheath 196 that is configured to accept the guidewire 18. The outer transverse dimension or cross sectional area of the obturator sheath 196 is configured to fill the gap between the side port 22 and the inner surface 164 of the inner lumen 13 of the stabilizer sheath 12 opposite the side port 22. Filling of the side port 22 by the obturator sheath 196 is illustrated in FIGS. 15 and 16 where the obturator sheath 196 is shown within the inner lumen 13 of the stabilizer sheath 12 passing over the abutment 60 of the side port 22 which forces a portion of it out of the side port 22 and extending distally within the inner lumen 13 of the stabilizer sheath 12 towards the distal end 156 of the stabilizer sheath 12. Guidewire 203 is shown disposed within the inner lumen 202 of the obturator sheath 196. FIG. 17 shows the distal end 200 of the obturator sheath 196 having a tapered configuration and showing the guidewire 203 disposed within and extending from the inner lumen 202 of the obturator sheath 196. Guidewire 203 may be a standard floppy tip guidewire used for interventional procedures. One embodiment of guidewire 203 is a floppy tip guidewire having a nominal outer diameter of about 0.036 inches to about 0.04 inches and a length of about 150 cm to about 200 cm. In another embodiment, guidewire 203 may be an exchange length guidewire having a length of about 250 cm to about 350 cm.

FIG. 17A illustrates an enlarged view in section of an alternative embodiment of a side port configuration of an embodiment of a stabilizer sheath 204. The guidewire 203 extending through the inner lumen 206 of the stabilizer sheath embodiment is maintained in a concentric arrangement with the longitudinal axis of the stabilizer sheath 204 by a sleeve portion 208 that is also shaped within the side port 210 to act as a deflective surface 212.

Figure 10:
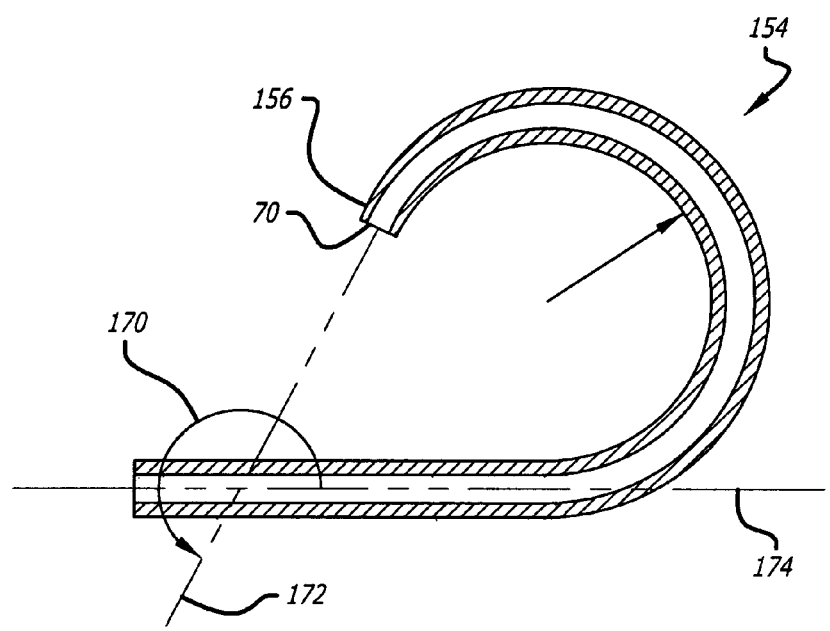
FIG. 10 is an enlarged view in longitudinal section of the distal most portion of the stabilizer sheath indicated by the encircled portion 10-10 in FIG. 6 an illustrating the curled curvature or "pig tail" of the distal most portion of the stabilizer sheath.
Figure 18:
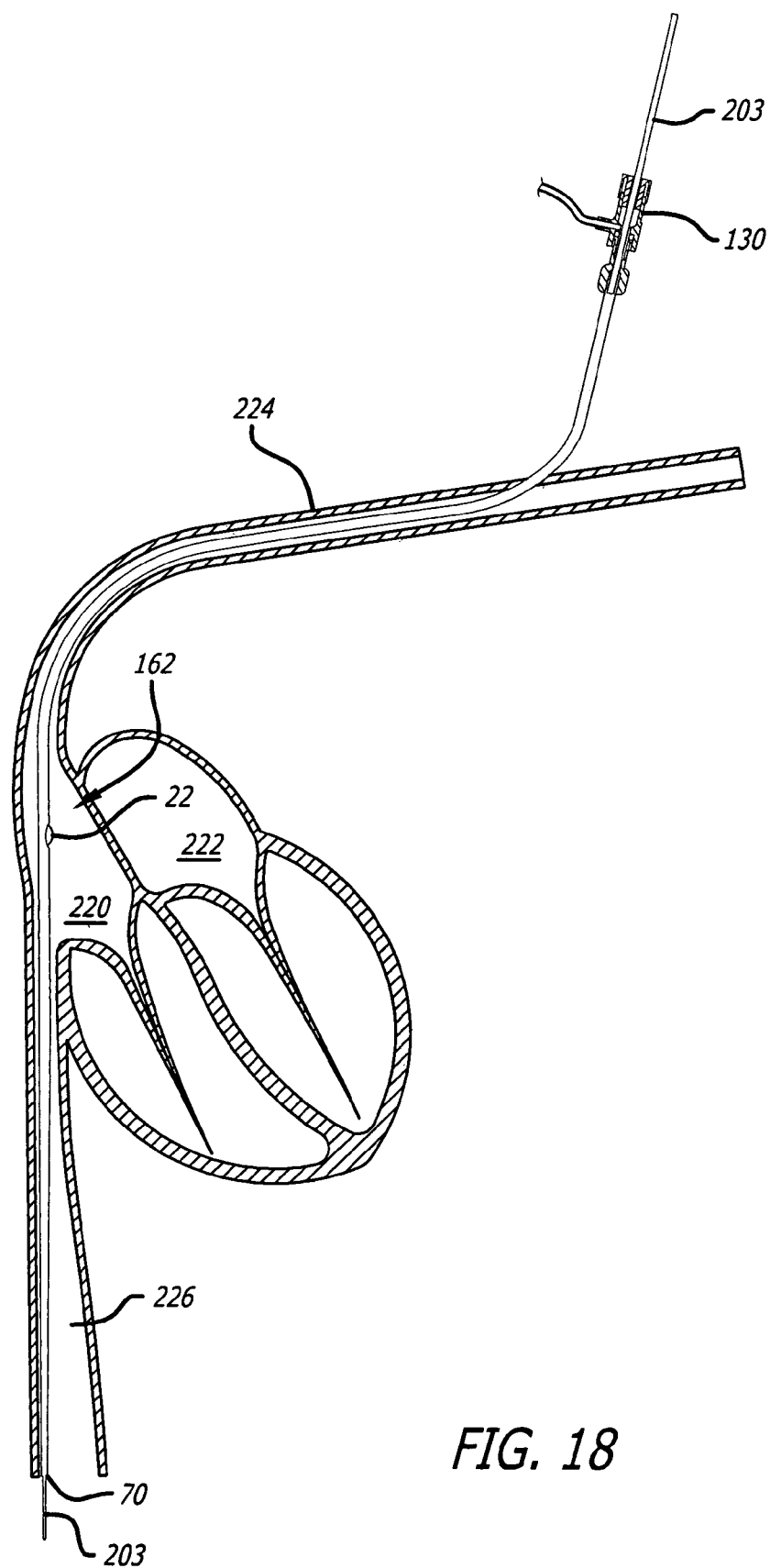
FIG. 18 shows a diagramatic view of the stabilizer sheath of the transmembrane access system of FIG. 1 being advanced into position over a guidewire with the distal end of the stabilizer sheath, which is being maintained is a straightened configuration by the guidewire, disposed within the inferior vena cava and the side port facing the right atrium of the patient. The obturator sheath is shown disposed within the inner lumen of the stabilizer sheath and is blocking the side port. The guidewire is also disposed within the inner lumen of the obturator sheath.

Referring to FIG. 18, embodiments of the transmembrane access system 10 may be used for a transseptal access procedure from the right atrium 220 of a patient's heart to the left atrium 222. In one embodiment, this procedure begins by placing a guidewire 203 into the patient's superior vena cava 224 through a needle inserted at a vascular access point such as a subclavian vein near the shoulder or a jugular vein on the neck, similar to a standard technique for placing pacemaker leads which is well known to skilled artisans. Thereafter, the distal port 70 of the stabilizer sheath 12 is then fed over the proximal end of the guidewire 203 which extends from the patient's body. The guidewire 203 is then advanced proximally through the inner lumen of the stabilizer sheath 12 until the proximal end of the guidewire 203 extends from the proximal end of the stabilizer sheath 12 or exits the optional guidewire port 68. The distal end of the obturator sheath 196 is then tracked over the proximal end of the guidewire 203 into the stabilizer sheath 12 until the obturator sheath 196 seats and comes to a stop. The distal end or pigtail portion 154 of the stabilizer sheath 12, which is maintained in a substantially straightened configuration by the stiffness of the guidewire 203, is tapered and thinned, as shown in FIG. 10, so that is serves as a dilator during insertion through the skin and into the vein. The stabilizer sheath 12 and obturator sheath 196 are then advanced distally together over the guidewire 18 into the superior vena cava of the patient. The stabilizer sheath 12 is advanced distally until the distal end 156 of the stabilizer sheath 12 is disposed within the inferior vena cava 226 and the side port 22 is within the right atrium 220 of the patient. Thereafter, the guidewire 203 and obturator sheath 196 are withdrawn from the inner lumen 13 of the stabilizer sheath 12, allowing the distal portion 154 of the stabilizer sheath 12 to assume its relaxed pigtail configuration, and allowing the guide catheter 14 and elongate tissue penetration device 16 to be advanced through the proximal adapter 130 of the stabilizer sheath 12 and through the inner lumen 13 of the stabilizer sheath 12 towards the side port 22.

This procedure may also be initiated from an access point from the patient's inferior vena cava 226 beginning by placing a guidewire into the patient's inferior vena cava through a needle inserted at a vascular access point such as a femoral vein near the groin, well known to skilled artisans. In the same manner described above for the superior vena cava approach, the proximal end of the guidewire 203 is backloaded into the stabilizer sheath 12, the obturator sheath 196 is advanced over the guide wire 203 into the stabilizer sheath until its distal end seats at the side port. The stabilizer sheath 12 and obturator sheath 196 are then inserted together over the guidewire 18 through the skin and into the vein, and then advanced distally together over the guidewire 18 through the inferior vena cava 226 of the patient until the distal end 156 of the stabilizer sheath 12 is disposed within the superior vena cava 224 and the side port 22 is disposed within the right atrium 220 of the patient.

FIG. 18 illustrates the stabilizer sheath 12 positioned through a chamber in the form of the right atrium 220 with the side port 22 of the stabilizer sheath 12 positioned in the chamber 220. The side port section 162 of the stabilizer sheath 12 spans the chamber 220 between a first orifice which is the opening of the superior vena cava 224 into the right atrium 220 and a second orifice which is the opening of the inferior vena cava 226 into the right atrium 220. The superior vena cava 224 and inferior vena cava 226 form two tubular structures extending from opposite sides of the chamber 220 which provide lateral support to the side port section 162 of the stabilizer sheath 12. The lateral support of the tubular structures 224 and 226 and respective orifices adjacent the side port section 162 of the stabilizer sheath 12 provides a stable platform from which the guide catheter 14 may be extended for performing procedures within the chamber 220. The lateral stability of the side port section provides back up support for the guide catheter 14 to be pushed or extended distally from the side port 22 and exert distal force against structures within the chamber 220 while maintaining positional control over the distal end of the guide catheter 14. This configuration provides the necessary stability and support for performing procedures within the chamber and beyond regardless of the size and shape of the chamber 220 which can vary greatly due to dilation or distortion caused by disease or other factors. This configuration contemplates lateral stabilization of the side port section 162 as a result of confinement of the stabilizer sheath portions adjacent the side port section 162 in respective tubular structures. However, a similar result could be achieved with a stabilizer sheath embodiment similar to stabilizer sheath 12 having a short distal section or no distal section extending distally from the side port section 22. For such an embodiment, stabilization of the side port section could be achieved by lateral or transverse confinement of a section of the stabilizer sheath proximal of the side port section in a tubular structure and lateral confinement of a guidewire extending distally from the inner lumen of the stabilizer sheath in a similar tubular structure.

Although the embodiment of the method illustrated in FIG. 18 is directed to a transseptal cardiac procedure, the stabilizer sheath 12 and guide catheter 14 arrangement could also be used for a variety of other indications depending on the shape of the guide or access catheter 14 used in conjunction with the stabilizer sheath 12. If the optional peel away tear line 167 is incorporated into the stabilizer sheath 12 and reinforcement member 166, applicable procedures could include deployment of pacing leads, e.g. into the coronary sinus for cardiac resynchronization therapy or biventricual pacing, placement of a prosthesis for mitral valve repair annulus repair as well as others. It will also be clear to the skilled artisan that the usefulness of the present invention is not limited to the venous circulation: many other anatomical areas, that may be accessed by catheter are advantageously accessed by making use of the added support and control provided by the side port stabilizer sheath and shaped guide catheter of this invention. A few additional examples include, but are not limited to: the coronary arteries via a stabilizer sheath with its side port very near its distal end as described above, or with a distal section designed with a "pig-tail" designed to pass through the aortic valve and into the left ventricle; retrograde access to the mitral valve and left atrium via the left ventricle using a stabilizer sheath with a short pigtail distal segment as described for the coronary arteries, but with its side port located more distally so that it may be placed in the mid left ventricle; and other areas, such as the renal arteries, where acute angles limit the control provided by conventional catheters.

Once in place, the stabilizer sheath 12 can be rotated within the chamber 220 to direct the side port 22 to any lateral direction within the chamber 220. The rotational freedom of the stabilizer sheath 12 within the chamber 220 can be combined with axial translation of the stabilizer sheath 12, in either a distal direction or proximal direction, to allow the side port 22 of the stabilizer sheath to be directed to most any portion of the chamber 220. When these features of the stabilizer sheath 12 are combined with a guide catheter 14 having a curved distal section extending from the side port 22, a subselective catheter configuration results whereby rotation, axial translation or both can be applied to the stabilizer sheath 12 and guide catheter 14 in order to access any portion of the interior of the chamber 220 from a variety of approach angles. The selectivity of the configuration is also discussed below with regard to FIGS. 24A-24C.

Figure 20:
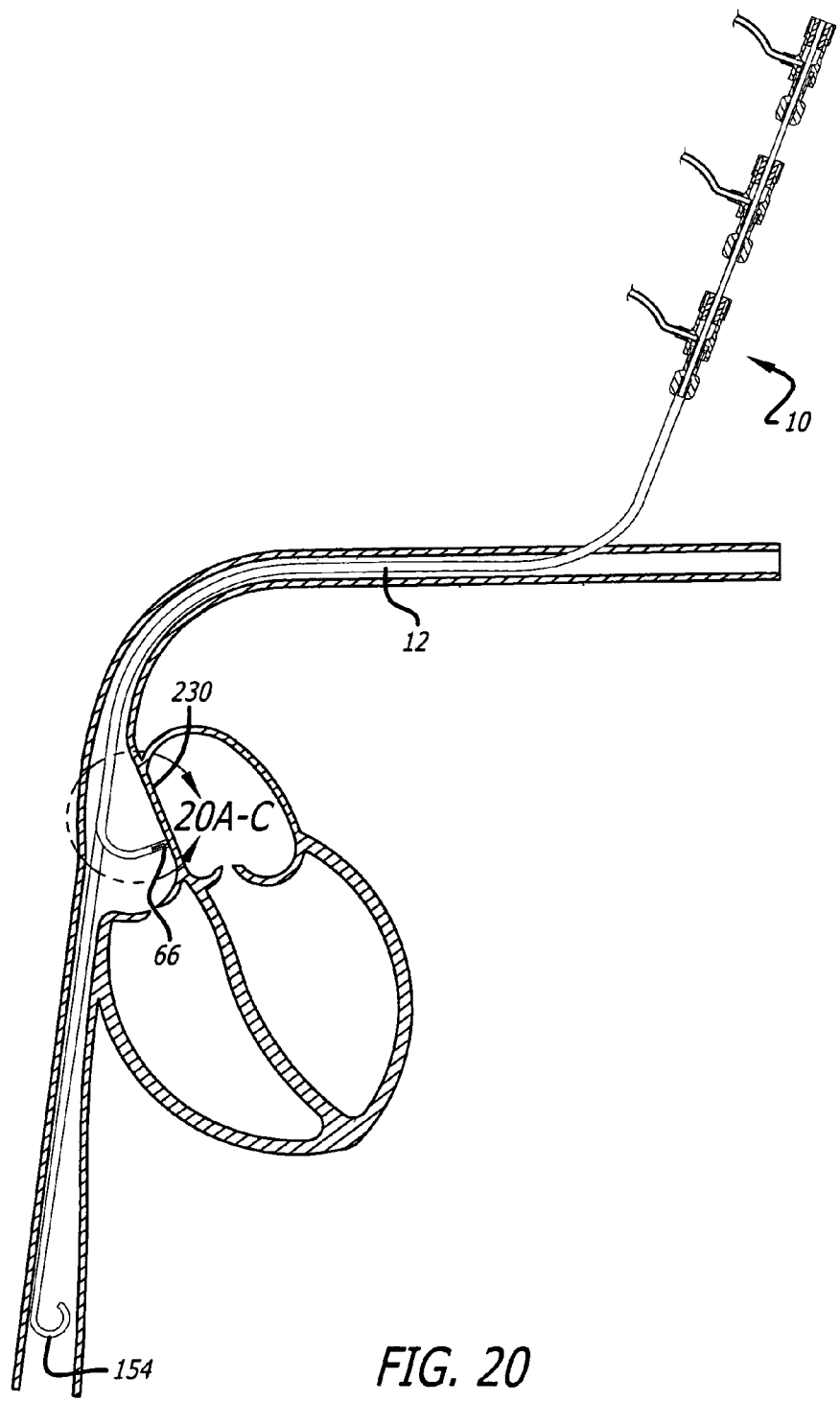
FIG. 20 shows the transmembrane system with the elongate tissue penetration device disposed within and extending from the guide catheter which is disposed within the inner lumen of the stabilizer sheath. The guide catheter distal end is extending radially from the side port of the stabilizer sheath and is positioned adjacent a desired area of the septum for access.

During insertion of the guide catheter 14 and elongate tissue penetration device 16, the tissue penetration member 32 of the elongate tissue penetration device 16 is disposed within the inner lumen of the distal portion 24 of the guide catheter 14 to prevent contact of the tissue penetration member 32 with the inner lumen 13 of the stabilizer sheath 12 during advancement. FIG. 19 shows an enlarged elevational view of the side port section 162 of the stabilizer sheath 12 with the distal end 66 of the guide catheter 14 and the distal end 38 of the tissue penetration device 32, disposed within the distal end 66 of the guide catheter, being advanced distally through the inner lumen 13 of the stabilizer sheath 12. As the guide catheter 14 and elongate tissue penetration device 16 continue to be advanced distally, the distal end 66 of the guide catheter 14 impinges on the deflective surface 62 of the abutment 60 opposite the side port 22. The distal section 24 of the guide catheter 14 then emerges from the side port 22 and begins to assume the pre-shaped configuration of the guide catheter 14. The pre-shaped configuration of the distal section 24 curves the distal end 66 of the guide catheter 14 away from the longitudinal axis 160 of the side port section 162 of the stabilizer sheath 12 and extends the distal end 66 of the guide catheter 14 radially from the side port 22 and against the septal wall 230 as shown in FIG. 20.

Figure 20A:
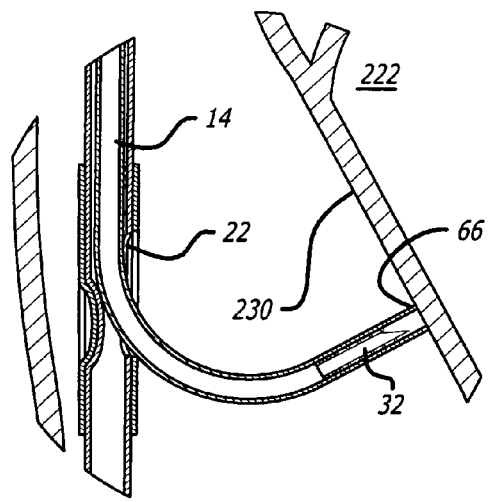
FIGS. 20A-20C illustrate a tissue penetration sequence by the tissue penetration member through the septum of the patient.
Figure 20B:
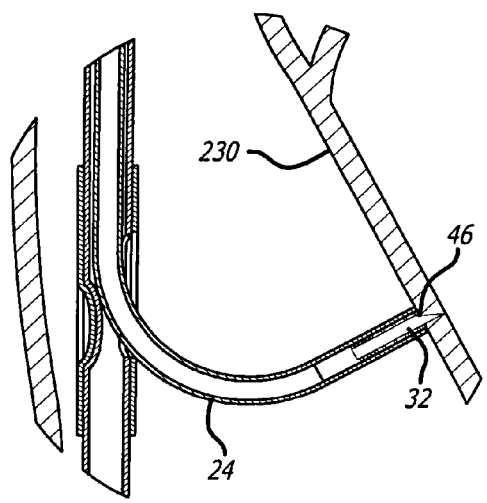
Figure 20C:
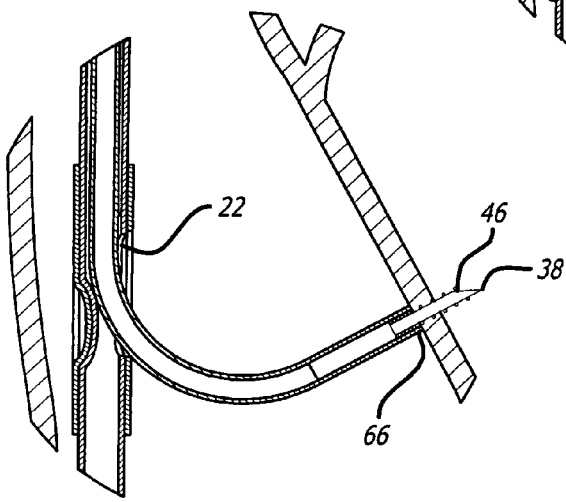

The distal end of the guide catheter 66 is advanced until it is positioned adjacent a desired area of the patient's septum 230 for transseptal access. In this arrangement, the orientation and angle of penetration or approach of the distal end 66 of the guide catheter 14 and elongate tissue penetration device 16 can be manipulated by axially advancing and retracting the stabilizer sheath 12 in combination with advancing and retracting the guide catheter 14 from the side port 22 of the stabilizer sheath 12. This procedure allows for access to a substantial portion of the patient's right atrial surface and allows for transmembrane procedures in areas other than the septum 230, and more specifically, the fossa ovalis of the septum 230. FIGS. 20A-20C illustrate a tissue penetration sequence by the tissue penetration member 32 through the septum of the patient. FIG. 20A shows an enlarged view of the distal end 66 of the guide catheter 14 disposed adjacent target tissue of the septal wall 230 with the tissue penetration member 32 withdrawn into the distal portion 24 of the guide catheter 14. FIG. 20B shows the tissue penetration member 32 during activation with the rotation of the tissue penetration member 32 causing the sharpened tip 38 of the tubular needle 34 to cut into and penetrate the septal wall 230 and allow advancement of the tubular needle 34. The sharpened distal end 46 of the helical tissue penetration member 42 penetrates tissue helically due to the rotational motive force of the tissue penetration member 32. The helical tissue penetration member 42 may also help pull the tubular needle 34 into the target tissue 230 as it advances. FIG. 20C shows the distal tip 38 of the tubular needle 34 having penetrated the septal wall 230 and in communication with the left atrium 222.

Figure 21:
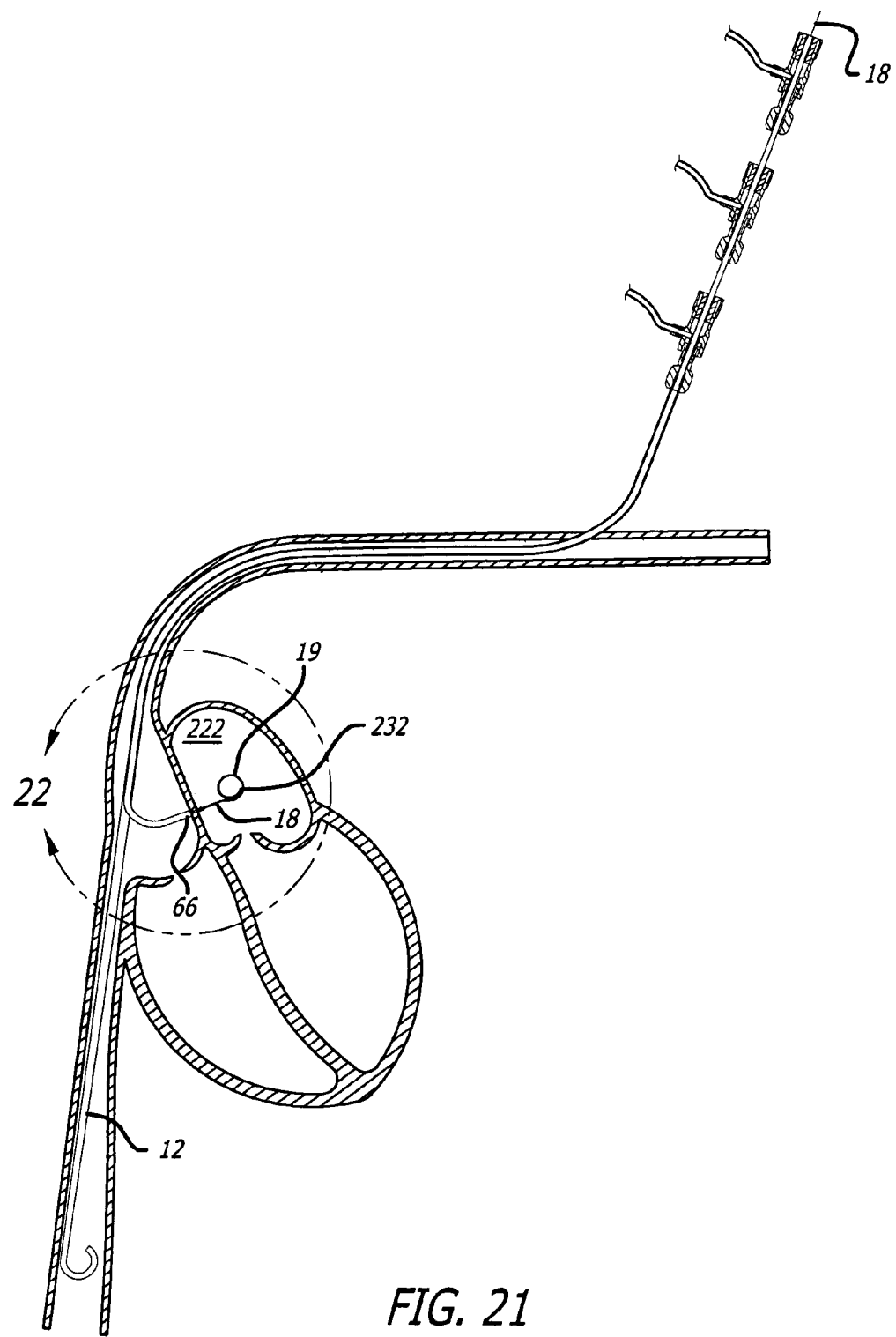
FIG. 21 illustrates the tissue penetration member having been activated by rotation of the torqueable shaft from a proximal portion of the torqueable shaft and having penetrated the septal wall of the patient's heart with the guidewire having been extended into the left atrium of the patient's heart.
Figure 22:
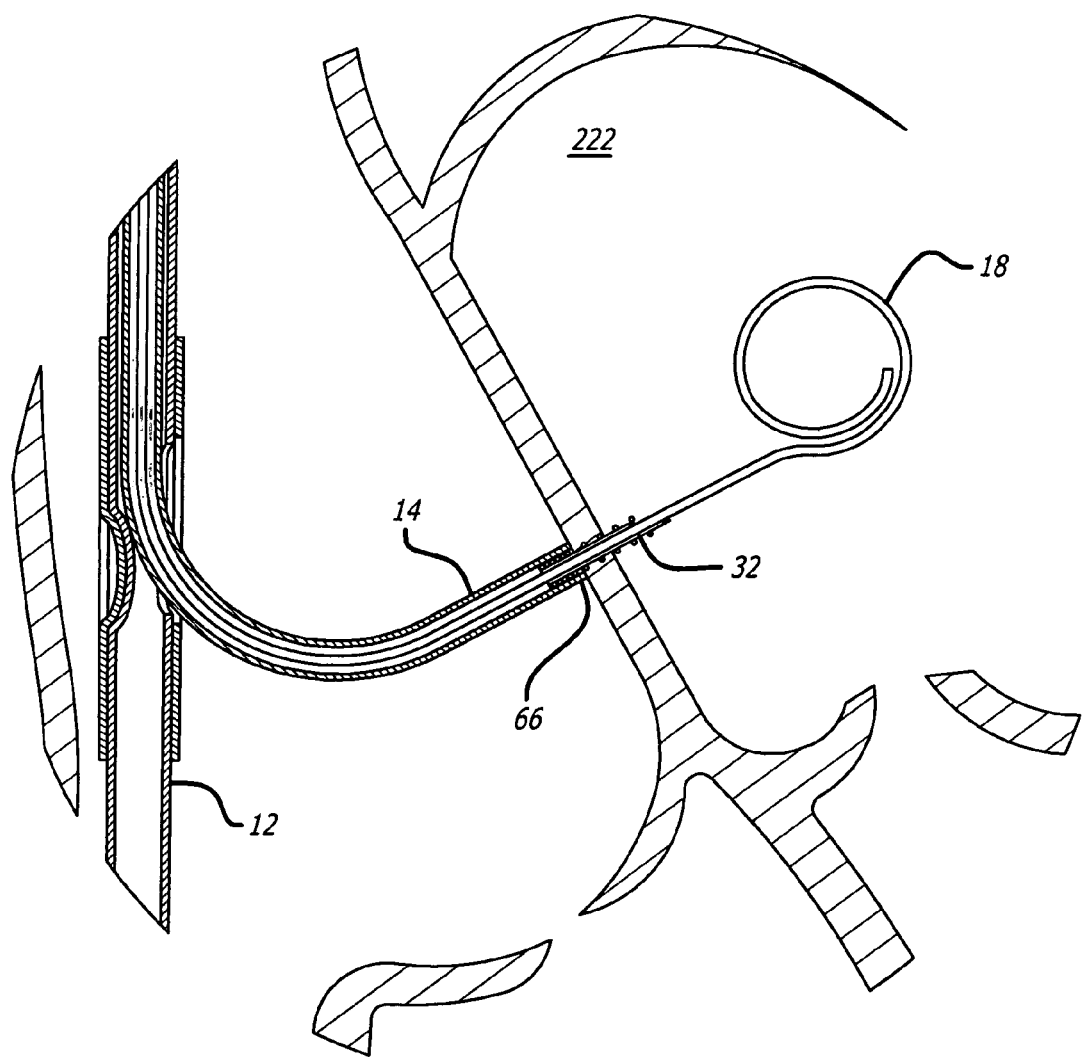
FIG. 22 is an enlarged view of the heart portion of FIG. 21.

Once the distal end 66 of the guide catheter 14 is disposed adjacent a desired area of target tissue, the tissue penetration member 32 of the elongate tissue penetration device 16 is advanced distally until contact is made between the sharpened tip 38 of the tubular needle 34 and the target tissue. The tissue penetration member 32 is then activated by rotation, axial movement or both, of the torqueable shaft 26 of the elongate tissue penetration device 16. As the tissue penetration member 32 is rotated, the sharpened tip 38 of the tubular needle 34 begins to cut into the target tissue 230 and the sharpened distal end 46 of the helical tissue penetration member 42 begins to penetrate into target tissue in a helical motion. As the sharpened tip 38 of the tubular needle 34 penetrates the target tissue, the tubular needle 34 provides lateral stabilization to the tissue penetration member 32 and particularly the helical tissue penetration member 42 during penetration. The rotation continues until the distal tip 38 of the tubular needle 34 perforates the septal membrane 230 and gains access to the left atrium 222 as shown in FIG. 21 and in an enlarged view in FIG. 22. Confirmation of access to the left atrium 222 can be achieved visually by injection of contrast media under fluoroscopy through the inner lumen 58 of the elongate tissue penetration device 16 from the side port 150 of the proximal adapter 134 of the elongate tissue penetration device 16. Confirmation can also be carried out by monitoring the internal pressure within the inner lumen of the elongate tissue penetration device 16 at the side port 150 of the proximal adapter 134 of the elongate tissue penetration device 16 during the rotation of the tissue penetration member 32.

Figure 23:
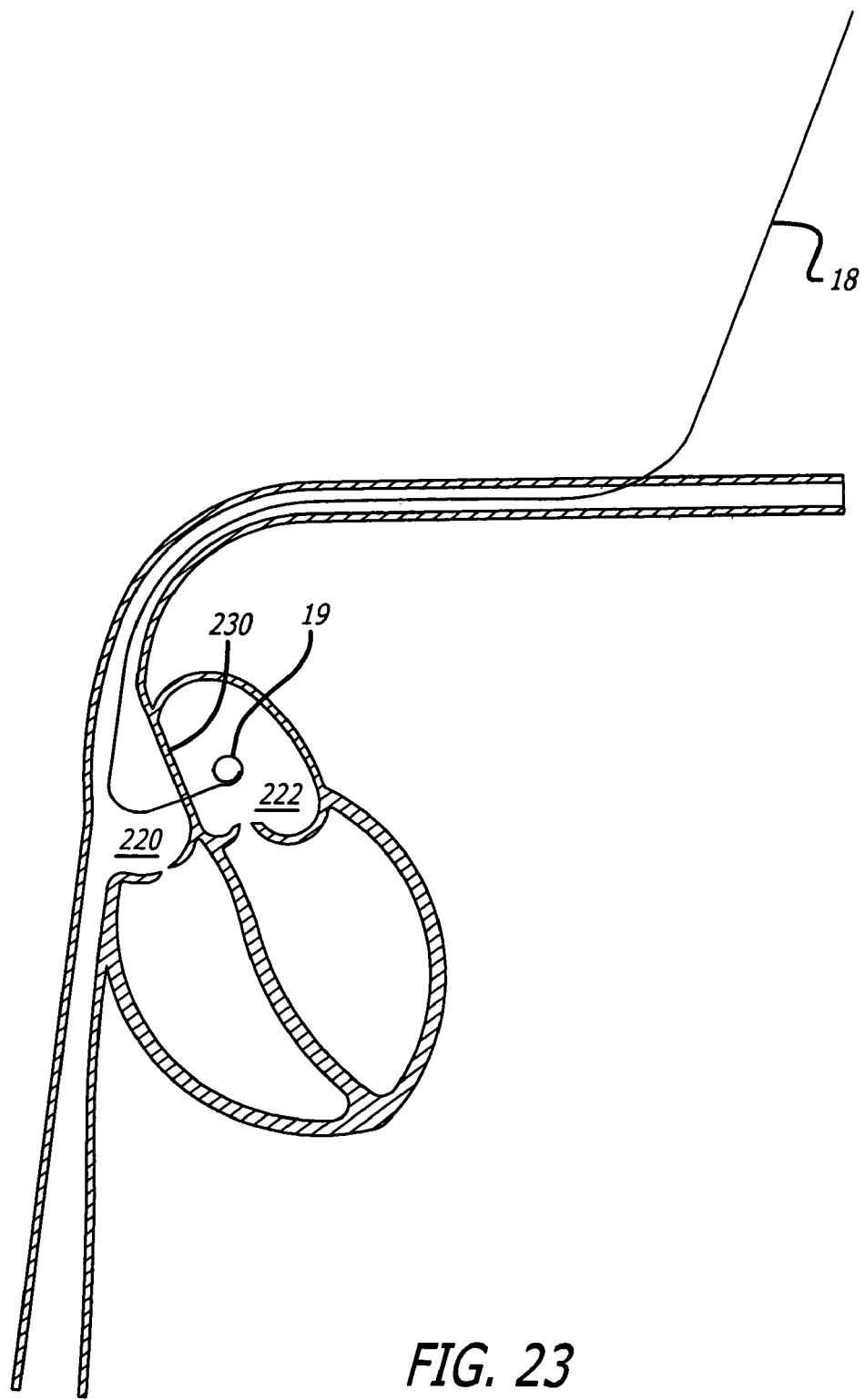
FIG. 23 shows the guidewire in position across the septal wall with the distal end of the guidewire in position in the left atrium after the stabilizer sheath, guide catheter and elongate tissue penetration device have been withdrawn proximally over the guidewire.

Once the tubular needle 34 has perforated the septal wall 230 and gained access to the left atrium 222, the guidewire 18 can then be advanced through the inner lumen 58 of the elongate tissue penetration device 16 and into the left atrium 222 opposite the membrane of the septum 230 of the right atrium 220. An embodiment of a guidewire 18 that may be useful for this type of transseptal procedure may be an Inoue wire, manufactured by TORAY Company, of JAPAN. This type of guidewire 18 may have a length of about 140 cm to about 180 cm, and a nominal transverse outer dimension of about 0.6 mm to about 0.8 mm. The distal section 19 of this guidewire 18 embodiment may be configured to be self coiling which produces an anchoring structure in the left atrium 222 after emerging from the distal port 40 of the tubular needle 34. The anchoring structure helps prevent inadvertent withdrawal of the guidewire 18 during removal of the guide catheter 14 and elongate tissue penetration device 16 once access across the tissue membrane 230 has been achieved. The guidewire 18 is shown in position across the septal wall 230 in FIGS. 22 and 23 with the distal end 232 of the guidewire 18 in position in the left atrium 222 after the stabilizer sheath 12, guide catheter 14 and elongate tissue penetration device 16 have been withdrawn proximally over the guidewire 18.

Figure 24A:
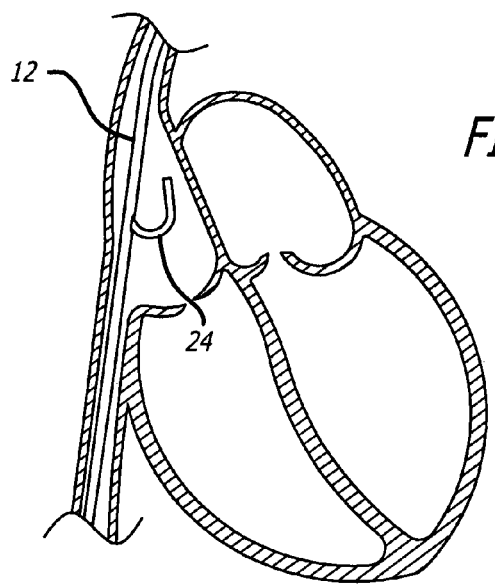
FIGS. 24A-24C illustrate how the orientation of the distal end of the guide catheter can be controlled by advancing and retracting the guide catheter within the side port of the stabilizer sheath, and axial movement of the stabilizer sheath relative to the right atrium.
Figure 24B:
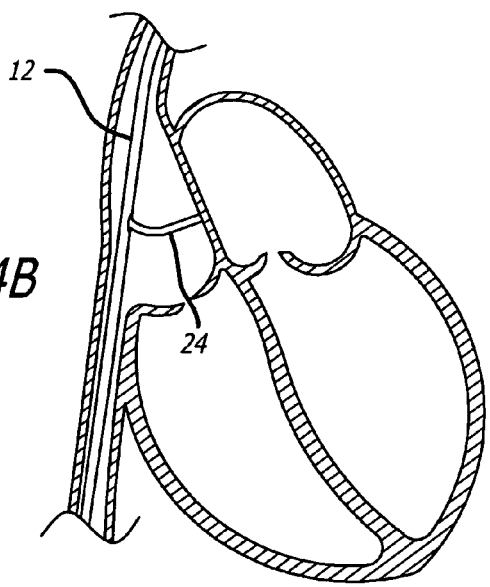
Figure 24C:
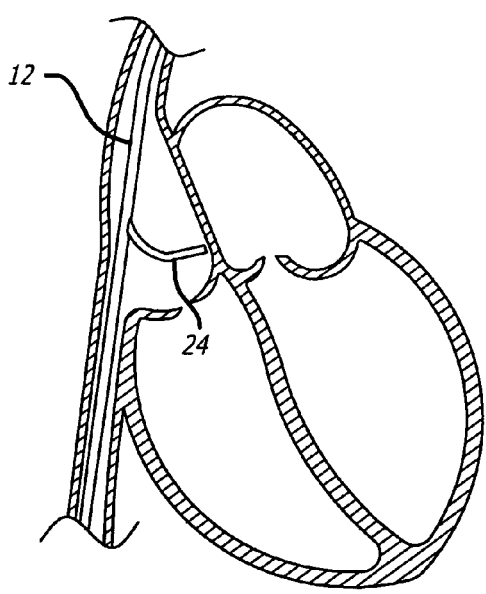

FIGS. 24A-24C illustrate how the orientation of the distal section 24 of the guide catheter 14 can be controlled by advancing and retracting the guide catheter 14 within the side port of the stabilizer sheath 12, and axial movement of the stabilizer sheath 12 relative to the right atrium 220. This arrangement and orientation technique can also be adapted to accessing other portions of the patient's anatomy. The tip angle and radius of curvature of the guide catheter 14 can be also be manipulated by pushing it against the surrounding anatomy.

Figure 25:
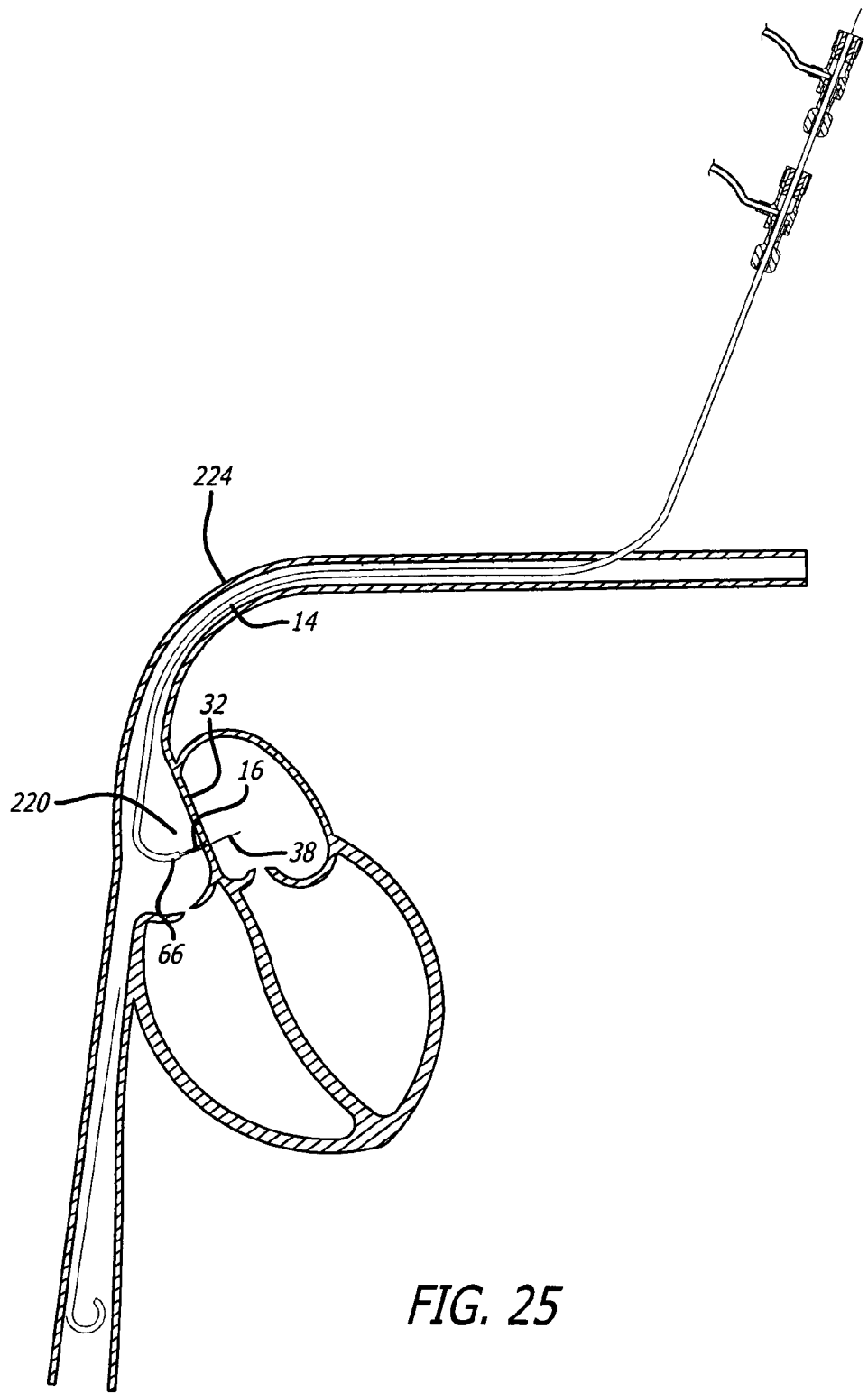
FIGS. 25 and 26 illustrate a method of transmembrane access across a patient's septal wall by using an embodiment of a guide catheter and elongate tissue penetration device having a tissue penetration member activated by rotation without the use of a stabilizer sheath.
Figure 26:
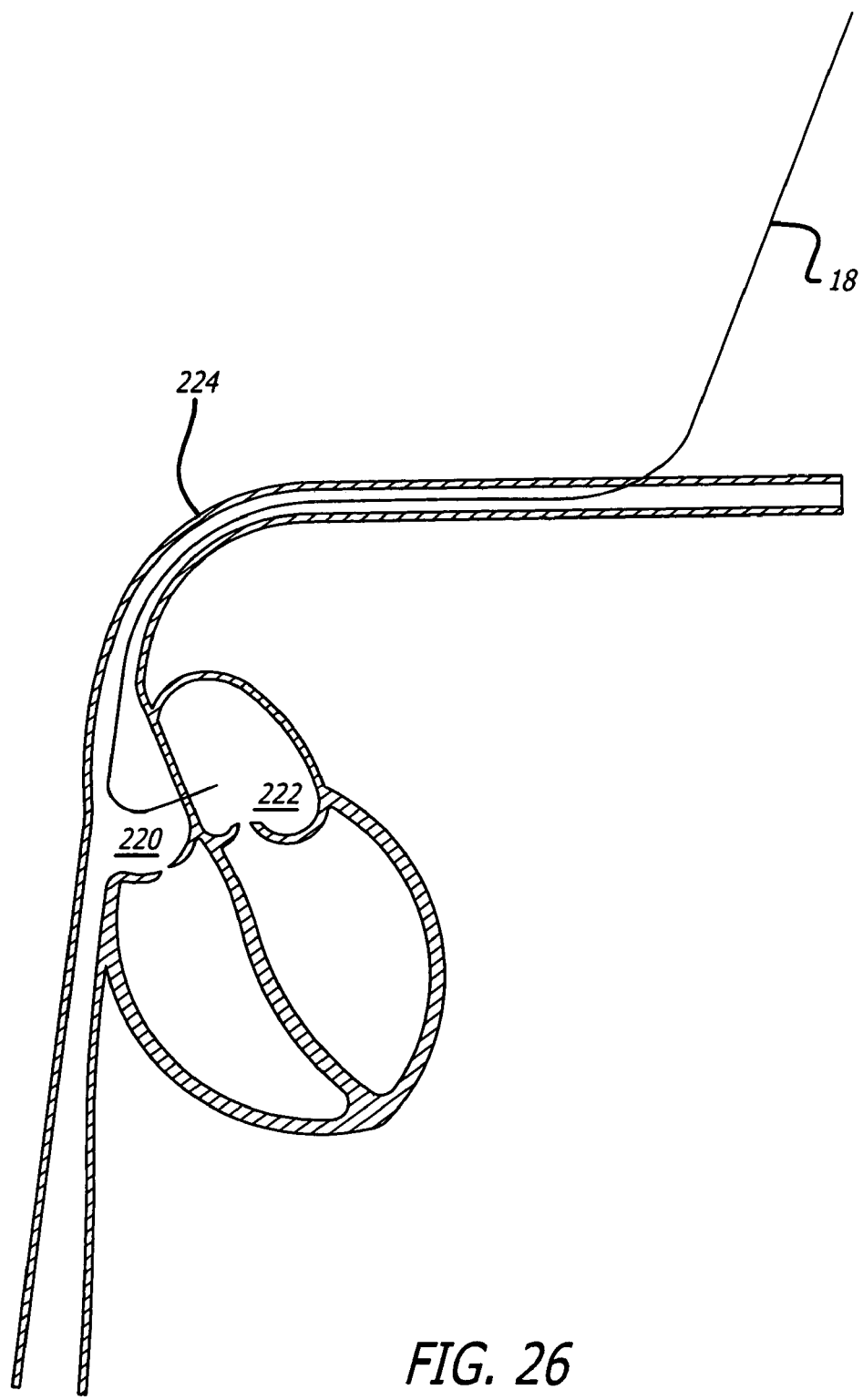

FIGS. 25 and 26 illustrate a method of transmembrane access across a patient's septal wall 230 by using an embodiment of a guide catheter 14 and elongate tissue penetration device 16 having a tissue penetration member 32 activated by rotation without the use of a stabilizer sheath 12. In this embodiment of use, the guide catheter 14 is advanced distally through the superior vena cava 224 of a patient and into the right atrium 220 over a guidewire 18. The guide catheter 14 is maneuvered until the distal end 66 of the guide catheter 14 is oriented towards a target area of the septum 230. The elongate tissue penetration device is then advanced distally from the distal end of the guide catheter until the sharpened distal tip 38 of the tissue penetration member 32 is in contact with the target tissue. The tissue penetration member 32 is then activated with rotational movement which causes the sharpened distal tip 38 of the tubular needle 34 and sharpened tip 46 of the helical tissue penetration member 42 of the tissue penetration member 32 to advance into the target tissue. Once the distal end 38 of the tubular needle 34 has penetrated the septum 230, as confirmed by either of the methods discussed above, the guidewire 18 is advanced distally through the inner lumen of the elongate tissue penetration device 16 and out of the distal end 40 of the tubular needle 34 and into the left atrial space 222. Thereafter, the elongate tissue penetration device 16 may be withdrawn proximally leaving the guidewire 18 in place across the septum 230 as shown in FIG. 26.

Figure 27:
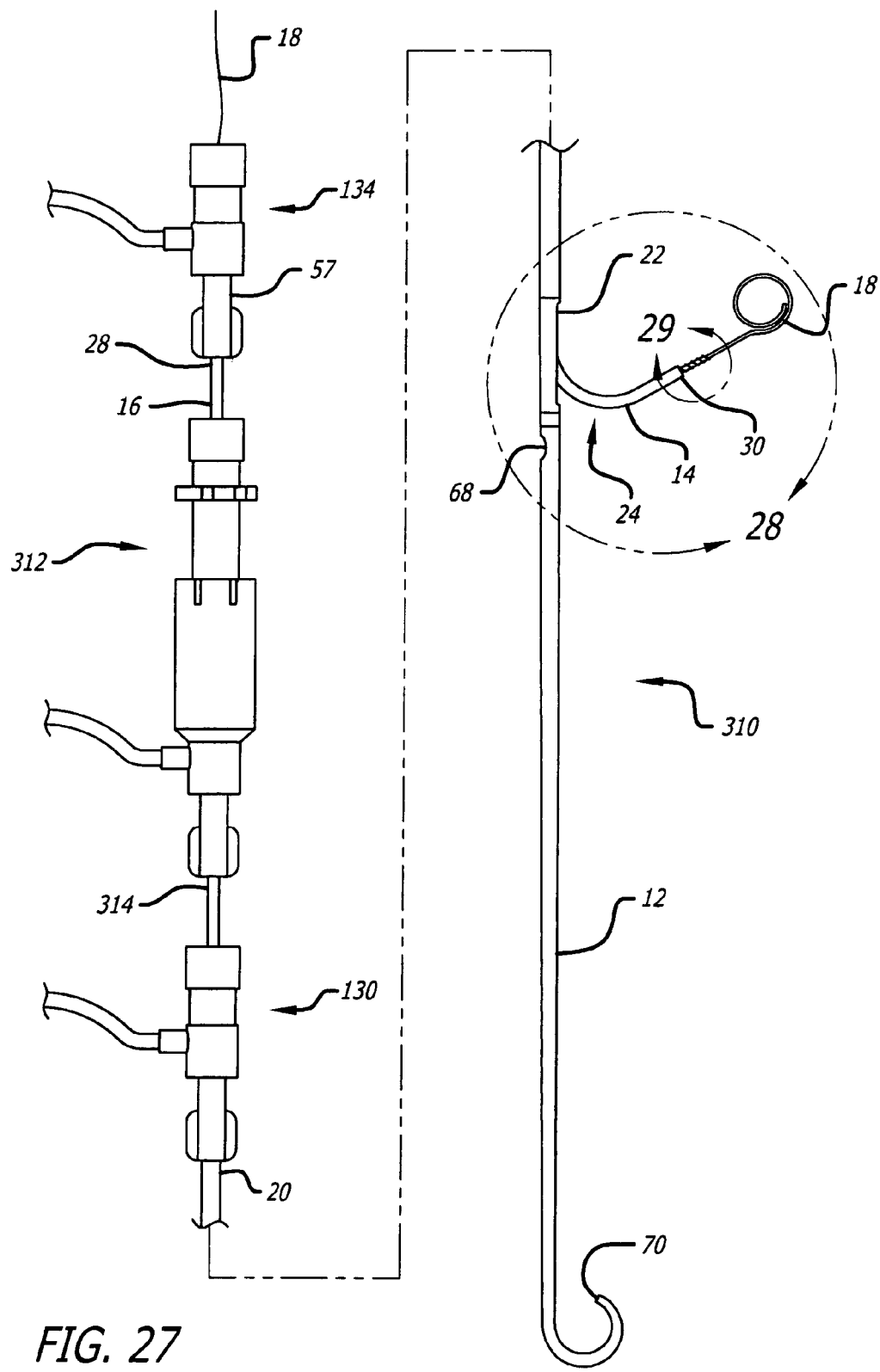
FIG. 27 is an elevational view of an alternative embodiment of a transmembrane access system that includes a proximal activation modulator.

FIG. 27 is an elevational view of an alternative embodiment of a transmembrane access system 310 that includes a proximal activation modulator 312 secured to a proximal end 314 of the guide catheter 14. Embodiments of the proximal activation modulator 312 may be configured to apply axial force while simultaneously advancing the device at an appropriate rate on the torqueable shaft, limit the number of rotations of the proximal end of the torqueable shaft 26 which controls the axial penetration of the tissue penetration member 32, or both of these functions as well as others. The system 310 shown in FIG. 27 includes a stabilizer sheath 12, a guide catheter 14, an elongate tissue penetration device 16 and a guidewire 18 disposed within an inner lumen of the elongate tissue penetration device 16. The stabilizer sheath 12 has a tubular configuration with an inner lumen 13 extending from a proximal end 20 of the stabilizer sheath 12 to a side port 22 disposed in the sheath 12. In one embodiment, the inner lumen 13 extends to the distal port 70 of the stabilizer sheath 12, and is open to one or more side ports 22 at one or more locations between the proximal end and distal end of the stabilizer sheath 12. The guide catheter 14 has a tubular configuration and is configured with an outer surface profile which allows the guide catheter 14 to be moved axially within the inner lumen of the stabilizer sheath 12. The guide catheter 14 has a shaped distal section 24 with a curved configuration in a relaxed state which can be straightened and advanced through the inner lumen of the stabilizer sheath 12 until it exits the side port 22 of the stabilizer sheath 12 as shown in more detail in FIG. 28.

Figure 29:
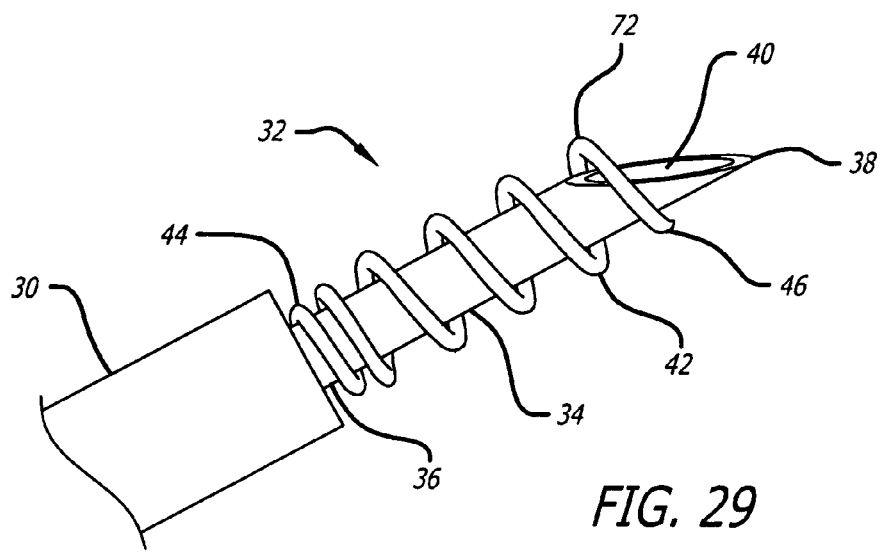
FIG. 29 is an enlarged view of the tissue penetration member secured to the torqueable shaft, indicated by the encircled portion 29-29 in FIG. 27.

The elongate tissue penetration device 16 includes a tubular flexible, torqueable shaft 26 having a proximal end 28, shown in FIG. 27, and a distal end 30. The distal end 30 of the torqueable shaft 26 is secured to a tissue penetration member 32, shown in more detail in FIG. 29, which is configured to penetrate tissue upon activation by rotation of the tissue penetration member 32. The tissue penetration member 32 has a tubular needle 34 with a proximal end 36, a sharpened distal end 38 and an inner lumen 40 that extends longitudinally through the tubular needle 34. A helical tissue penetration member 42 has a proximal end 44 and a sharpened distal end 46 and is disposed about the tubular needle 34. The helical tissue penetration member 42 has an inner diameter which is larger than an outer diameter of the tubular needle 34 so as to leave a gap between the tubular needle 34 and the helical tissue penetration member 42 for the portion of the helical tissue penetration 42 that extends distally from the distal end 30 of the torqueable shaft 26.

Figure 28:
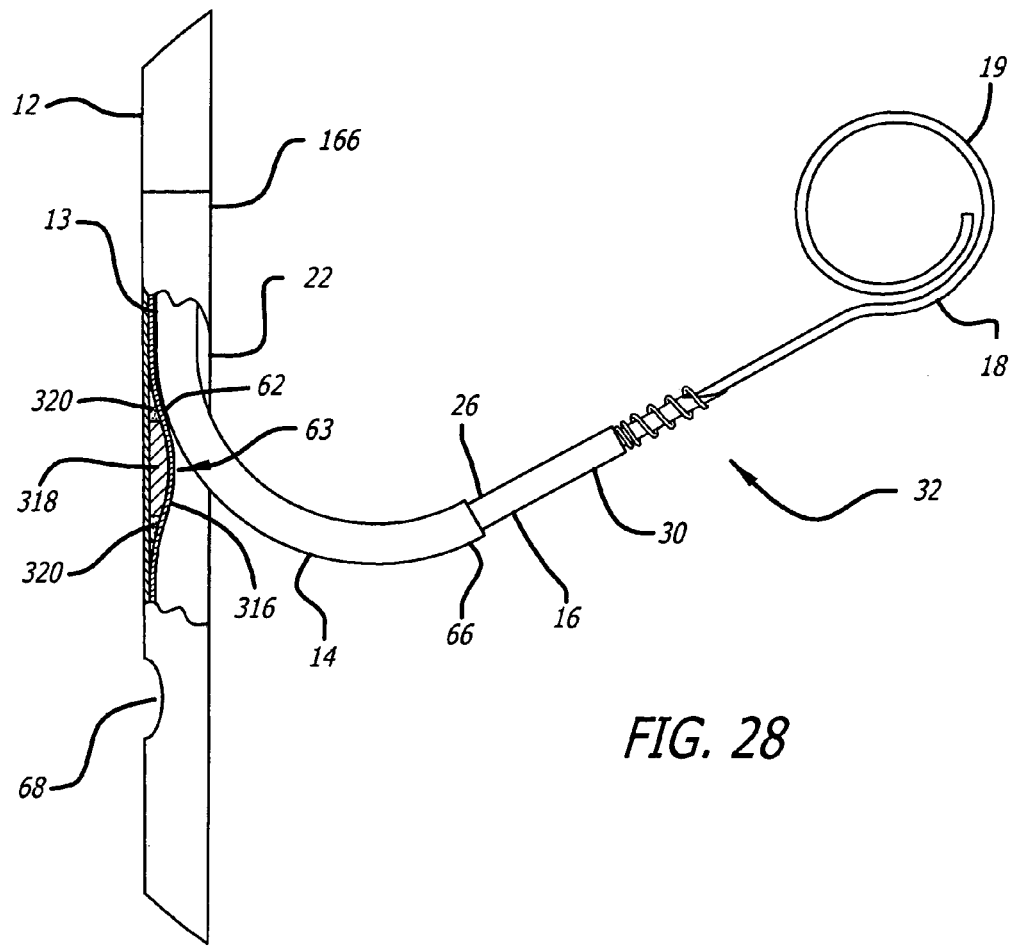
FIG. 28 is an enlarged view in partial section of the side port portion of the transmembrane access system of FIG. 27 indicated by the encircled portion 28-28 of FIG. 27.

Referring to FIG. 28, an abutment 316 having a radially deflective surface 62 is disposed within the inner lumen 13 of the stabilizer sheath 12 opposite the side port 22 of the sheath 12. In the embodiment shown, the apex 63 of the abutment 316 is disposed towards the distal end of the side port 22 which disposes the deflective surface 62 in a position which is longitudinally centered, or substantially longitudinally centered, in the side port 22. This configuration allows for reliable egress of the distal end 66 of the guide catheter 14 from the side port 22 after lateral deflection of the guide catheter 14 by the deflective surface 62. The deflective surface 62 of the abutment 316 serves to deflect the distal end 66 of the guide catheter 14 from a nominal axial path and out of the side port 22 during advancement of the guide catheter 14 through the inner lumen 13 of the stabilizer sheath 12. The abutment 316 is formed from a section of solid dowel pin 318 disposed between an inner surface of the tubular reinforcement member 166 and an outer surface of the stabilizer sheath 12. The solid dowel pin 318 is secured in place by epoxy potting material 320, but may be secured in place by a variety of other methods including mechanical capture or solvent bonding.

Figure 29A:
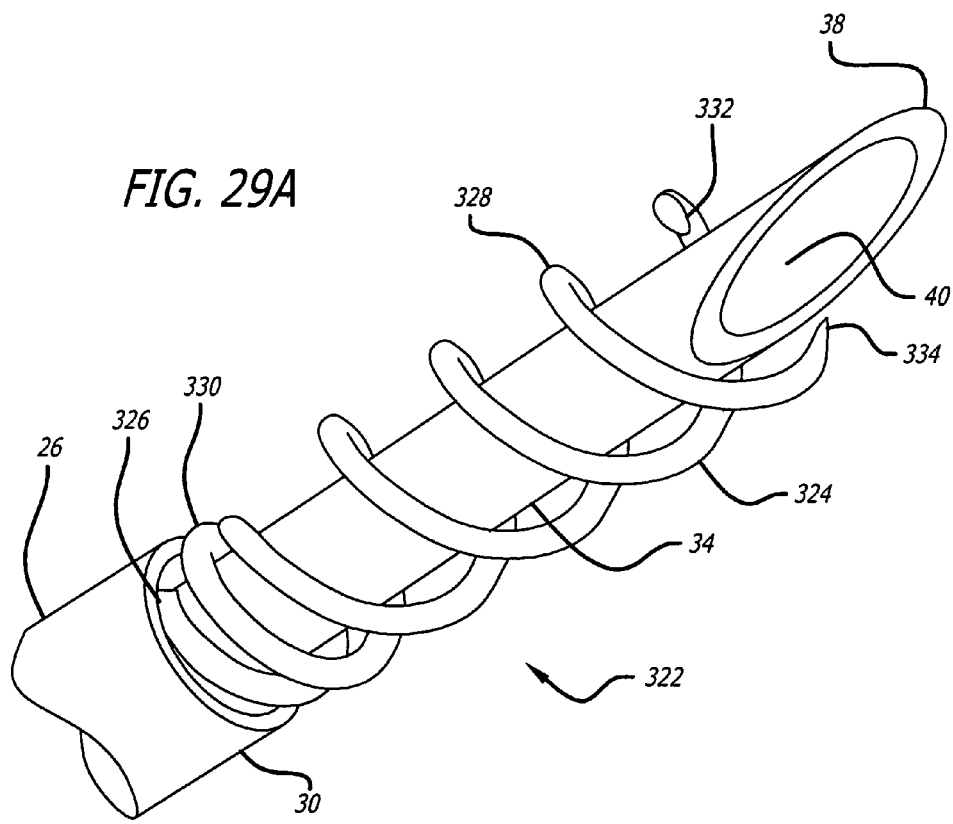
FIG. 29A is an enlarged view of an alternative embodiment of a tissue penetration member having two helical tissue penetration members.
Figure 30:
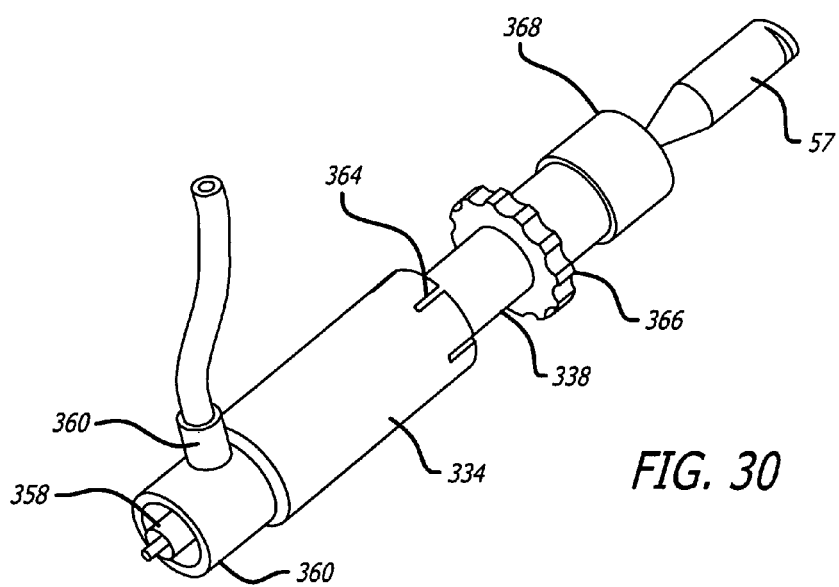
FIG. 30 is a perspective view of an embodiment of an activation modulator for applying controlled axial movement to the tissue penetration member and limiting the rotational movement of the tissue penetration member.
Figures 31, 32:
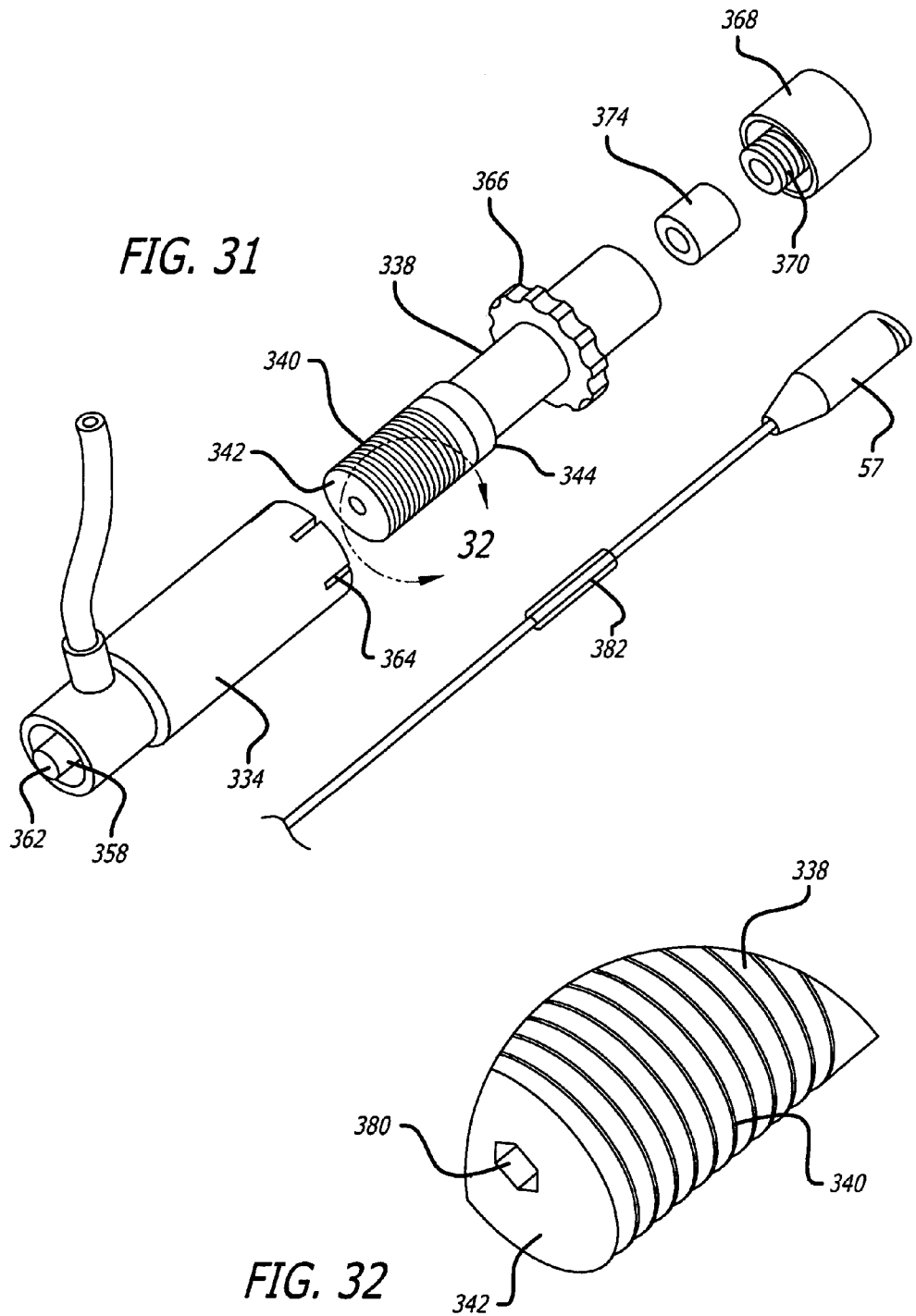
FIG. 31 is an exploded view of the activation modulator and proximal section of the torqueable shaft of the transmembrane access system of FIG. 27.
FIG. 32 is an enlarged view of a distal portion of the threaded inner barrel of the activation modulator.
Figure 33:
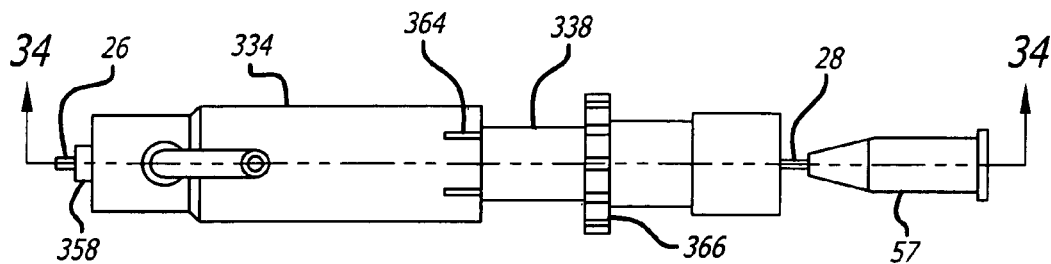
FIG. 33 is an elevational view of the activation modulator of FIG. 30.

FIG. 29A is an enlarged view of an alternative embodiment of a tissue penetration member 322 having two helical tissue penetration members. The tissue penetration member has a tubular needle 34 secured to a distal end 30 of the torqueable shaft 26. A first helical tissue penetration member 324 has a proximal end 326 secured to the tubular needle 34 and distal end 30 of the torqueable shaft 26. A second helical tissue penetration member 328 has a proximal end 330 secured to the tubular needle 34 and distal end 30 of the torqueable shaft 26. The first helical tissue penetration member 324 has a sharpened distal tip 332 configured to penetrate tissue upon rotation of the tissue penetration member 322. The second helical tissue penetration member 328 has a sharpened distal tip 334 configured to penetrate tissue upon rotation of the tissue penetration member 322. The first and second helical tissue penetration members 324 and 328 provide opposing forces which cancel each other to a certain extent and minimize the lateral deflection of the tissue penetration member 322 during rotation and tissue penetration member 322. Sharpened distal tips 332 and 334 of the helical tissue penetration members 324 and 328 are disposed opposite the tubular needle 34 180 degrees apart and oriented such that the sharpened tips 332 and 334 are disposed about 90 degrees from the distal extremity of the sharpened tip 38 of the tubular needle 34.

Figure 34:
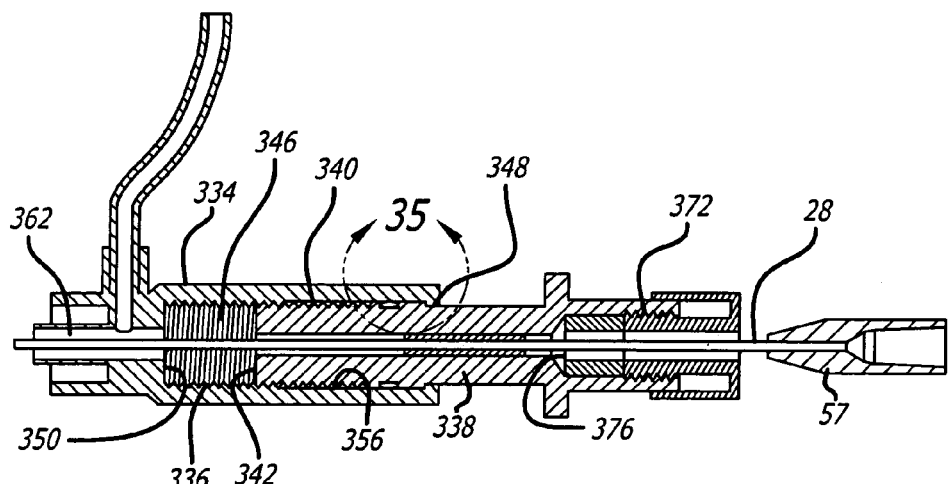
FIG. 34 is an elevational view in longitudinal section of the activation modulator of FIG. 33 taken along lines 34-34 of FIG. 33 showing the threaded inner barrel disposed at a proximal limit of axial movement.
Figure 35:
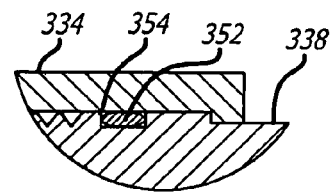
FIG. 35 is an enlarged view of the rotation seal disposed about the threaded inner barrel of the activation modulator indicated by the encircled portion 35-35 of FIG. 34.
Figure 36:
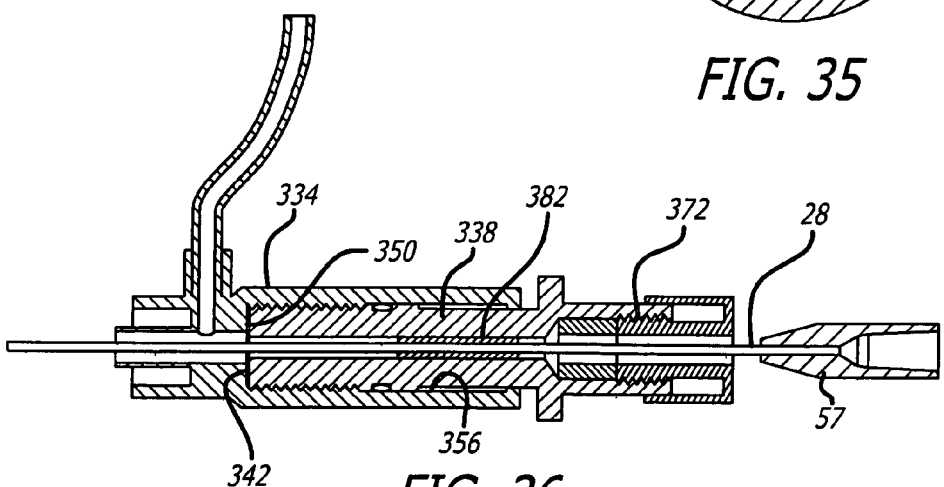
FIG. 36 is an elevational view in longitudinal section of the activation modulator of FIG. 34 with the threaded inner barrel disposed at a distal limit of axial movement.

FIGS. 30-36 illustrate the activation modulator 312 for applying controlled axial movement and rotation to the tissue penetration member 32 and limiting the rotational movement of the tissue penetration member 32. The activation modulator 312 has a fixed member in the form of an outer barrel 334 which has a threaded portion 336 shown if FIG. 34. A rotating member in the form of an inner barrel 338 has a threaded portion 340 that is engaged with the threaded portion 336 of the outer barrel 334. The inner barrel 338 has a distal surface 342 and annular flange 344 which are axially captured within a cavity 346 of the outer barrel 334 shown in FIG. 34. FIG. 34 shows the threaded inner barrel 340 disposed at a proximal limit of axial movement wherein a proximal surface of the annular flange 344 is engaged with a distal surface of an annular flange 348 of the outer barrel 334. FIG. 36 shows the threaded inner barrel 338 disposed at a distal limit of axial movement with the distal surface 342 engaged with a distal cavity surface 350 of the outer barrel 334. The distance from distal surface 342 to distal cavity surface 350 controls or limits the depth of penetration of the tissue penetration member 32.

FIG. 35 is an enlarged view of the rotation seal 352 of the inner barrel 338 disposed within an annular groove 354 of the threaded inner barrel. The rotation seal 352 may be an annular seal such as an o-ring type seal that is secured within the annular groove 354 and is sized to seal against an inner surface 356 of the proximal portion of the cavity 346 of the outer barrel 334. The rotation seal 352 provides a fluid seal between the outer surface of the inner barrel 338 and the cavity 346 while allowing relative rotational movement between the inner barrel 338 and outer barrel 334.

The outer barrel 334 has a substantially tubular configuration with a Luer type fitting 358 at the distal end 360 of the outer barrel 334. The Luer fitting 358 can be used to secure the activation modulator 312 in a fluid tight arrangement to a standard guide catheter 14 having a mating Luer connector arrangement on a distal end thereof. The outer barrel 334 also has a side port 360 which is in fluid communication with an inner lumen 362 disposed within the distal end of the outer barrel 334. The side port 360 can be used to access the space between the outer surface of the torqueable shaft 26 and inner surface of the guide catheter lumen for injection of contrast media and the like. The outer barrel 334 has a series of longitudinal slots 364 that allow the annular flange 348 portion of the outer barrel 334 to expand radially for assembly of the inner barrel 338 into the cavity 346 of the outer barrel 334.

The inner barrel 338 has a knurled ring 366 that may be useful for gripping by a user in order to manually apply torque to the inner barrel 338 relative to the outer barrel 334. A threaded compression cap 368 having a threaded portion 370 is configured to engage a threaded portion 372 of the inner barrel 338, as shown in FIG. 34. The compression cap 368 has an inner lumen to accept the torqueable shaft 26 of the tissue penetration device. A sealing gland 374 having a substantially tubular configuration and an inner lumen configured to accept the torqueable shaft 26 is disposed within a proximal cavity 376 of the inner barrel 338 and can be compressed by the compression cap 368 within the proximal cavity 376 such that the sealing gland 374 forms a seal between an inner surface of the proximal cavity 376 and an outer surface of the torqueable shaft 26. The compressed sealing gland 374 also provides mechanical coupling between the inner barrel 338 and the torqueable shaft 26 so as to prevent relative axial movement between the torqueable shaft 26 and the inner barrel 338. The sealing gland may be made from any suitable elastomeric material that is sufficiently deformable to provide a seal between the proximal cavity 376 and the torqueable shaft 26. A distal inner lumen 380 of the inner barrel 338 is keyed with a hexagonal shape for the transverse cross section of the inner lumen 380 which mates with a hexagonal member 382 secured to the outer surface of a proximal portion of the torqueable shaft 26 so as to allow relative axial movement between the hexagonal member 382 and the inner lumen 380 but preventing relative rotational movement. This arrangement prevents rotational and axial slippage between the inner barrel 338 and the torqueable shaft 26 during rotational activation of the activation modulator 312.

Axial movement or force on the tissue penetration member is generated by the activation modulator 312 upon relative rotation of the inner barrel 338 relative to the outer barrel 334. The axial movement and force is then transferred to the tissue penetration member 32 by the torqueable shaft 26. The pitch of the threaded portions may be matched to the pitch of the helical tissue penetration member 42 so that the tissue penetration member 32 is forced distally at a rate or velocity consistent with the rotational velocity and pitch of the helical tissue penetration member 42.

For use of the transmembrane access system 310, the distal end of the guide catheter 14 is positioned adjacent a desired target tissue site in a manner similar to or the same as discussed above with regard to the transmembrane access system 10. The tissue penetration member 32 of the tissue penetration device is then advanced until the distal tip 38 of the tissue penetration member 32 is disposed adjacent target tissue. The torqueable shaft 26 is then secured to the inner barrel 338 of the activation modulator 312 by the sealing gland 374 with the inner barrel disposed at a proximal position within the cavity 346 of the outer barrel 334. The user then grasps the knurled ring 366 and rotates the ring 366 relative to the outer barrel 334 which both rotates and advances both the inner barrel 338 relative to the outer barrel 334. This activation also rotates and distally advances the torqueable shaft 26 and tissue penetration member 32 relative to the guide catheter 14. The rotational activation of the activation modulator can be continued until the distal surface 342 of the inner barrel 338 comes into contact with the surface 350 of the outer barrel 334. The axial length of the cavity 346 can be selected to provide the desired number of maximum rotations and axial advancement of the torqueable shaft 26 and tissue penetration member 32. In one embodiment, the maximum number of rotations of the inner barrel 338 relative to the outer barrel 334 can be from about 4 rotations to about 10 rotations.

Figure 37:
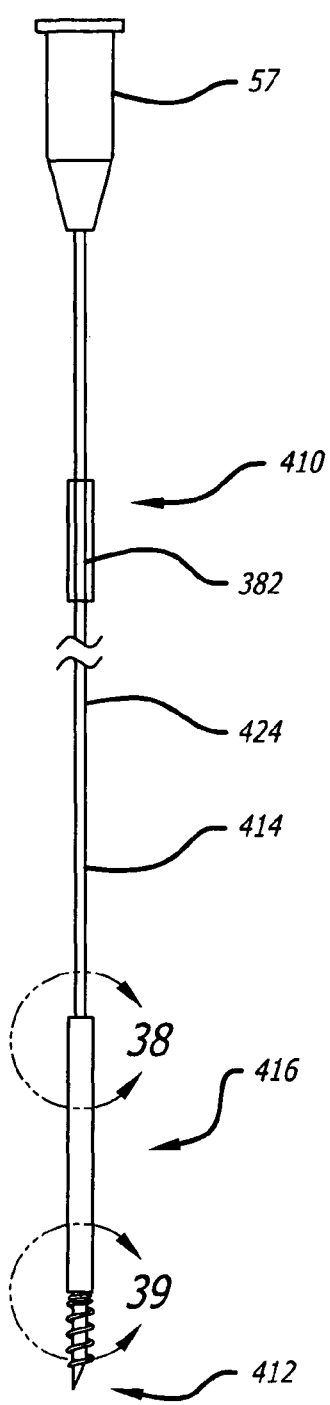
FIG. 37 is an elevational view, partially broken away, of an alternative embodiment of a tissue penetration device.
Figure 38:
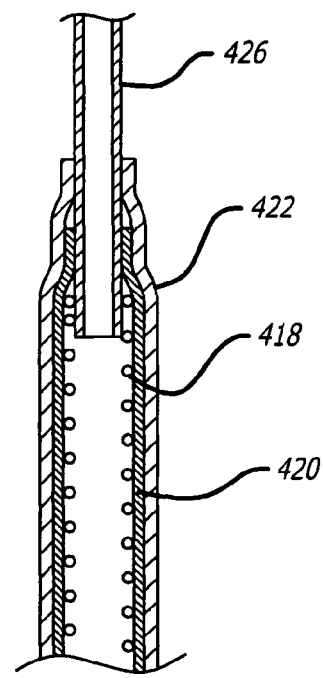
FIG. 38 is an enlarged view in longitudinal section of the tissue penetration device of FIG. 37 indicated by the encircled portion 38-38 in FIG. 37.
Figure 39:
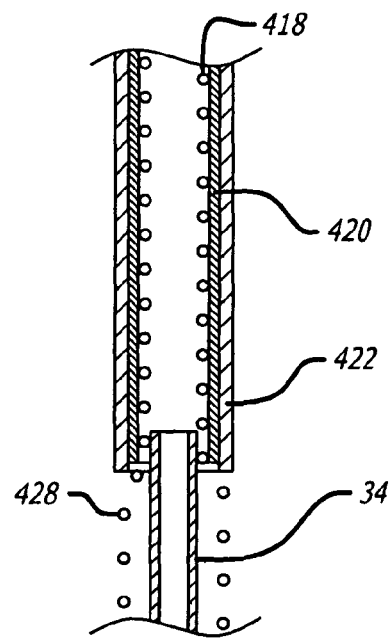
FIG. 39 is an enlarged view in longitudinal section of the tissue penetration device of FIG. 37 indicated by the encircled portion 39-39 in FIG. 37.

The tissue penetration device 16 discussed above may have a variety of configurations and constructions. FIGS. 37-39 illustrate an alternative embodiment of a tissue penetration device 410. The tissue penetration device 410 has a construction and configuration that is similar in some ways to the tissue penetration device 16 discussed above. The tissue penetration device 410 has a tissue penetration member 412 secured to a distal end of a torqueable shaft 414. A keyed hexagonal member 382 is secured to a proximal portion of the torqueable shaft 414 for coupling with the activation modulator 312 discussed above. The distal portion 416 of the tissue penetration device 410 has a flexible construction that includes a helical coil member 418 disposed within a braided tubular member 420, both of which are covered by a polymer sheath 422 that provides a fluid tight lumen to contain fluids passing therethrough. The proximal portion of the torqueable shaft 414 is made from a tubular member 424 of high strength material, such as a hypodermic tubing of stainless steel. The distal end 426 of the tubular member is secured to the proximal ends of the helical coil member 416 and braided tubular member 420 by any suitable method such as soldering, brazing, welding, adhesive bonding or the like.

A tubular needle 34 forms the center of the tissue penetration member 412 along with the distal portion 428 of the helical coil member 418 which is configured as a helical tissue penetration member disposed about the tubular needle 34. The proximal end 430 of the tubular needle 34 is secured to the helical coil member 418 and braided tubular member 420 by any suitable method such as soldering, brazing, welding, adhesive bonding or the like. The polymer sheath 422 may be bonded to the outer surface of the braided tubular member 420 or mechanically secured to the braided tubular member by methods such as heat shrinking the polymer sheath material over the braided tubular member 420. The flexible distal section 416 can have any suitable length. In one embodiment, the flexible distal section has a length of about 15 cm to about 40 cm. The configuration, dimensions and materials of the tissue penetration member 412 can be the same as or similar to the configuration, dimensions and materials of the tissue penetration members 32 and 322 discussed above.

FIGS. 40-42 illustrate yet another alternative embodiment of a tissue penetration device 430 having a construction similar to that of the tissue penetration device 410 except that the tubular member 432 of the torqueable shaft 434 extends continuously from the proximal end 436 of the device 430 to the distal end 438 and the helical coil member 418 of the tissue penetration device 410 has been replaced with a flexible section 438 of the tubular member 432. The flexible section 438 is made by producing a series of adjacent alternating partial transverse cuts into the tubular member 432 so as to allow improved longitudinal flexibility of the tubular member 432 in the flexible section 438 while maintaining the radial strength of the tubular member 432. The flexible section 438 is covered by a braided tubular member 440 and a polymer sheath 442. The braided tubular member 440 may be secured at its proximal end and distal end 444 by soldering, brazing, welding, adhesive bonding or the like. The polymer sheath 442 may be secured by adhesive bonding, thermal shrinking or the like. The tissue penetration member 446 includes a helical tissue penetration member 448 secured at its proximal end to the tubular member 432 which terminates distally with a sharpened tip 448 in a configuration similar to the tissue penetration members discussed above. The configuration, dimensions and materials of the tissue penetration member 446 can be the same as or similar to the configuration, dimensions and materials of the tissue penetration members 32 and 322 discussed above.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the invention. Accordingly, it is not intended that the invention be limited by the forgoing detailed description.

We claim:

1. A transmembrane access system, comprising:
    a stabilizer sheath including a tubular configuration with an inner lumen extending therein and including a side port which is disposed on a distal section of the sheath, which is configured to allow passage of a guide catheter therethrough and which is in communication with the inner lumen;
    a tubular guide catheter including a shaped distal section that has a curved configuration in a relaxed state and an outer surface which is configured to move axially within a portion of the inner lumen of the stabilizer sheath that extends from the proximal end of the stabilizer sheath to the side port;
    a tissue penetration member which is configured to move axially within an inner lumen of the tubular guide catheter and which is axially extendable from the guide catheter for membrane penetration and
    an obturator sheath comprising an elongate tubular member having an inner lumen configured to accommodate axial movement of a guidewire therein and having an outer surface profile that is configured to occupy the inner lumen and side port of the stabilizer sheath during initial deployment of the stabilizer sheath in a patient's body.

2. The system of claim 1 wherein the tissue penetration member is configured to penetrate tissue upon rotation and the system further comprising an elongate torqueable shaft coupled to the tissue penetration member, a tubular needle with a sharpened distal end and an inner lumen, a helical tissue penetration member disposed about the hypodermic needle and a torqueable shaft having a distal end secured to a proximal portion of the hypodermic needle and a proximal portion of the helical tissue penetration member.

3. The system of claim 2 wherein the torqueable shaft comprises a tubular member having an inner lumen disposed therein and configured to allow passage of a guidewire and wherein the inner lumen of the torqueable shaft is in fluid communication with the inner lumen of the tubular needle.

4. A stabilizer sheath system, comprising
    an elongate tubular shaft having an inner lumen;
    a side port disposed in a distal section of the elongate tubular shaft in fluid communication with the inner lumen and a distal portion of the distal section comprising a curled section wherein the discharge axis of the distal end of the elongate tubular shaft is greater than 180 degrees from the longitudinal axis of the elongate tubular shaft proximal of the curled section;
    a mechanical reinforcement member disposed at the side port; and
    a deflecting surface disposed in the inner lumen opposite the side port.

5. The stabilizer sheath system of claim 4 further comprising an obturator sheath comprising an elongate tubular member having an inner lumen configured to accommodate axial movement of a guidewire therein and having an outer surface profile that is configured to occupy the inner lumen and side port of the stabilizer sheath during initial deployment of the stabilizer sheath in a patient's body.

6. A method of positioning an access catheter within a chamber of a patient's body, comprising
    providing an access system, including:
        a stabilizer sheath having a tubular configuration with an inner lumen extending therein and having a side port disposed on a distal section of the sheath and in communication with the inner lumen; and
        a tubular access catheter having a shaped distal section that has a curved configuration in a relaxed state and an outer surface which is configured to move axially within a portion of the inner lumen of the
    stabilizer sheath that extends from the proximal end of the stabilizer sheath to the side port;
    advancing the stabilizer sheath through a first tubular structure of the patient which is in fluid communication with the chamber and positioning the stabilizer sheath with the side port of the stabilizer sheath within the chamber of the patient's body and with a portion of the stabilizer sheath distal of the side port into a second tubular structure which is also in fluid communication with the chamber;
    advancing the distal end of the access catheter through the inner lumen of the stabilizer sheath until the distal end of the access catheter exits the side port of the stabilizer sheath; and
    rotating the stabilizer sheath and axially translating the access catheter until the distal end of the access catheter is positioned adjacent a desired site of the chamber.

7. The method of claim 6 wherein the access system further comprises an obturator sheath having an elongate tubular member having an inner lumen configured to accommodate axial movement of a guidewire therein and having an outer surface profile that is configured to occupy the inner lumen and side port of the stabilizer sheath during initial deployment of the stabilizer sheath into the patient's body and wherein the stabilizer sheath is advanced into position in the chamber with the obturator disposed within the inner lumen of the stabilizer sheath and a guidewire within the inner lumen of the obturator.

* * * * *